(12) United States Patent
Ruat et al.

(10) Patent No.: US 8,981,149 B2
(45) Date of Patent: Mar. 17, 2015

(54) COMPOUNDS MODULATING THE HEDGEHOG PROTEIN SIGNALING PATHWAY, MARKED FORMS THEREOF, AND APPLICATIONS

(71) Applicants: Centre National De La Recherche Scientifique, Paris (FR); Universite De Strasbourg, Strasbourg (FR)

(72) Inventors: Martial Ruat, Orsay (FR); Hélène Faure, Gif-sur-Yvette (FR); Hermine Roudaut, Marly-la-Ville (FR); Lucile Hoch, Auffargis (FR); Angèle Schoenfelder, Lampertheim (FR); Maurizio Taddei, Monteriggioni (IT); André Mann, Ostwald (FR)

(73) Assignees: Centre National de la Recherche Scientifique, Paris (FR); Universite de Strasbourg, Strasbourg (FR)

( * ) Notice: Subject to any disclaimer, the term of this patent is extended or adjusted under 35 U.S.C. 154(b) by 0 days.

(21) Appl. No.: 14/346,538

(22) PCT Filed: Sep. 21, 2012

(86) PCT No.: PCT/IB2012/055033
§ 371 (c)(1),
(2) Date: Mar. 21, 2014

(87) PCT Pub. No.: WO2013/042082
PCT Pub. Date: Mar. 28, 2013

(65) Prior Publication Data
US 2014/0228441 A1    Aug. 14, 2014

(30) Foreign Application Priority Data
Sep. 23, 2011 (FR) ...................................... 11 58519

(51) Int. Cl.
| | | |
|---|---|---|
| C07C 279/24 | (2006.01) | |
| A61K 31/165 | (2006.01) | |
| C07C 279/22 | (2006.01) | |
| G01N 33/50 | (2006.01) | |
| G01N 33/574 | (2006.01) | |

(52) U.S. Cl.
CPC ............ *C07C 279/24* (2013.01); *C07C 279/22* (2013.01); *G01N 33/5011* (2013.01); *G01N 33/5041* (2013.01); *G01N 33/57492* (2013.01)
USPC ............ 564/158; 564/176; 514/616; 514/622

(58) Field of Classification Search
USPC .......................... 564/158, 176; 514/616, 622
See application file for complete search history.

(56) References Cited

U.S. PATENT DOCUMENTS

| | | | |
|---|---|---|---|
| 6,291,516 B1 | 9/2001 | Dudek et al. | |
| 6,432,970 B2 | 8/2002 | Beachy et al. | |
| 2005/0282231 A1 | 12/2005 | Tabin et al. | |
| 2007/0060546 A1 | 3/2007 | Ruat et al. | |
| 2007/0218775 A1 | 9/2007 | Coronado | |
| 2009/0005416 A1 | 1/2009 | Munchhof et al. | |
| 2009/0281089 A1 | 11/2009 | Gunzner et al. | |
| 2011/0275663 A1* | 11/2011 | Ruat et al. ..................... 514/300 |
| 2012/0196865 A1 | 8/2012 | Ruat et al. | |

FOREIGN PATENT DOCUMENTS

| | | |
|---|---|---|
| FR | 2 850 022 A1 | 7/2004 |
| RU | 38486 U1 | 6/2004 |
| WO | WO-99/52534 A1 | 10/1999 |
| WO | WO-00/41545 A2 | 7/2000 |
| WO | WO-01/19800 A2 | 3/2001 |
| WO | WO-01/27135 A2 | 4/2001 |
| WO | WO-01/74344 A2 | 10/2001 |
| WO | WO-01/98344 A2 | 12/2001 |
| WO | WO-02/30421 A2 | 4/2002 |

(Continued)

OTHER PUBLICATIONS

Amatore et al.; "Direct Method for Carbon—Carbon Bond Formation: The Functional Group Tolerant Cobalt-Catalyzed Alkylation of Aryl Halides;"Chem. Eur. J., vol. 16, No. 20; p. 5848-5852; dated May 2010; abstract retrieved on May 9, 2014 from <http://onlinelibrary.wiley.com/doi/10.1002/chem.201000178/abstract>.

Berman et al.; "Medulloblastoma Growth Inhibition by Hedgehog Pathway Blockade;"Science, vol. 297, No. 5586; pp. 1559-1561; dated Aug. 2002; abstract retrieved on May 9, 2014 from <http://www.sciencemag.org/content/297/5586/1559.abstract>.

Borzillo et al.; "The Hedgehog Signaling Pathway as a Target for Anticancer Drug Discovery;"Curr. Top Med. Chem., vol. 5, No. 2; pp. 147-157; dated 2005; abstract retrieved on May 9, 2014 from <http://benthamscience.com/journal/abstracts.php?journalID—ctme&articleID=79030>.

Buonamici et al.; "Interfering with Resistance to Smoothened Antagonists by Inhibition of the PI3K Pathway in Medulloblastoma;"Sci. Transl. Med. vol. 2, No. 51; pp. 51-70; dated Sep. 2010; retrieved on May 19, 2014 from <https://www.researchgate.net/publication/46820535_Interfering_with_resistance_to_smoothened_antagonists_by_inhibition_of_the_PI3K_pathway_in_medulloblastoma>.

(Continued)

Primary Examiner — Shailendra Kumar
(74) Attorney, Agent, or Firm — Alston & Bird LLP

(57) ABSTRACT

The invention relates to compounds of formula (I), and the use thereof as a drug, particularly for the treatment of tumors associated with hyperactivation of the hedgehog protein signaling pathway, treatment of neurodegenerative diseases, treatment of diseases related to cerebral development (holoprosencephaly), for stem cell monitoring treatment of cerebrovascular accidents and cardiovascular accidents, treatment of diseases involving oligodendrocytes and diseases involving neurolemmocytes, for application thereof in vitro for modulating human or animal stem cell renewal, and for the treatment of diabetes. The invention also relates to pharmaceutical compositions having a compound of formula (I). The invention also relates to a method for radio-marking compounds having formula (I), the marked compounds, and the use of the compounds as research tools, and method for screening and/or identifying ligands in the Smoothened receptor (Smo) binding sites, methods for identifying agonists and antagonists of the Smoothened receptor, and a method for identifying cells.

13 Claims, 5 Drawing Sheets

(56) References Cited

FOREIGN PATENT DOCUMENTS

| WO | WO-02/30462 A2 | 4/2002 |
|---|---|---|
| WO | WO-2006/028958 A2 | 3/2006 |
| WO | WO-2006/080894 A2 | 8/2006 |
| WO | WO-2007/059157 A1 | 5/2007 |
| WO | WO-2008/075196 A1 | 6/2008 |
| WO | WO-2009/130422 A2 | 10/2009 |
| WO | WO-2011/010013 A1 | 1/2011 |
| WO | WO-01/26644 A2 | 4/2011 |

OTHER PUBLICATIONS

Chen et al.; "Inhibition of Hedgehog signaling by direct binding of cyclopamine to Smoothened;"Genes Dev., vol. 16, No. 21; pp. 2743-2748; dated Nov. 2002; retrieved on May 9, 2014 from <http://genesdev.cshlp.org/content/16/21/2743.full.pdf+html>.

Chen et al.; "Small molecule modulation of Smoothened activity;"PNAS, vol. 99, No. 22; pp. 14071-14076; dated Oct. 2002; retrieved on May 9, 2014 from <http://www.pnas.org/content/99/22/14071.full.pdf+html>.

Dessaud et al.; "Pattern formation in the vertebrate neural tube: a sonic hedgehog morphogen-regulated transcriptional network;" Development, vol. 135, No. 15; pp. 2489-2503; dated Aug. 2008; retrieved on May 9, 2014 from <http://dev.biologists.org/content/135/15/2489.full.pdf+html>.

Dessole et al.; "Discovery of N-[(1-aryl-1H-indazol-5-yl)methyl]amides derivatives as smoothened antagonists for inhibition of the hedgehog pathway;"Bioorg. & Med. Chem. Lett., vol. 19, No. 15; pp. 4191-4195; dated Aug. 2009; abstract retrieved on May 9, 2014 from <http://www.sciencedirect.com/science/article/pii/S0960894X09008178>.

Dijkgraaf et al.; "Small Molecule Inhibition of GDC-0449 Refractory Smoothened Mutants and Downstream Mechanisms of Drug Resistance;" Cancer Res., vol. 71, No. 2; pp. 435-444; dated 2011; retrieved on May 9, 2014 from <http://cancerres.aacrjournals.org/content/71/2/435.full.pdf+html>.

Frank-Kamenetsky et al.; "Small-molecule modulators of Hedgehog signaling: identification and characterization of Smoothened agonists and antagonists ;" J. Biol., vol. 1, No. 10; pp. 1-19; dated Nov. 2002; retrieved on May 9, 2014 from <http://jbiol.com/content/pdf/1475-4924-1-10.pdf>.

Heretsch et al.; "Modulators of the hedgehog signaling pathway;"Bioorg. & Med. Chem., vol. 18, No. 18; pp. 6613-6624; dated Sep. 2010; abstract retrieved on May 9, 2014 from <http://www.sciencedirect.com/science/article/pii/S0968089610006917>.

Herwijnen et al.; "Meta Selectivity in the Friedel—Crafts Reaction Induced by a Faujasite-Type Zeolite ;" J. Org. Chem., vol. 66, No. 8; p. 2874-2876; dated Apr. 2001; abstract retrieved on May 9, 2014 from <http://pubs.acs.org/doi/abs/10.1021/jo005716r>.

Incardona et al.; "The teratogenic *Veratrum* alkaloid cyclopamine inhibits sonic hedgehog signal transduction;"Development, vol. 125, No. 18; p. 3553-3562; dated Sep. 1998; retrieved on May, 9, 2014 form <http://dev .biologists.org/content/125/18/3553.full.pdf+html>.

Ingham et al.; "Select this articleHedgehog signaling in animal development: paradigms and principles;"Genes Dev., vol. 15, No. 23; pp. 3059-3087; dated Dec. 2001; retrieved on May 9, 2014 from <http://genesdev.cshlp.org/content/15/23/3059.full.pdf+html>.

Luo et al.; "Superior Effect of a π-Acceptor Ligand (Phosphine—Electron-Deficient Olefin Ligand) in the Negishi Coupling Involving Alkylzinc Reagents;" Org. Lett., vol. 9, No. 22; pp. 4571-4574; dated Oct. 2007; abstract retrieved on May 9, 2014 from <http://pubs.acs.org/doi/abs/10.1021/ol701995t>.

Low et al.; "Clinical Experience With Hedgehog Pathway Inhibitors;" J. Clin. Oncol., vol. 28, No. 38; pp. 5321-5326; dated Dec. 2010; retrieved on May 9, 2014 from <http://jco.ascopubs.org/content/28/36/5321.full.pdf+html?sid=98e0c5f3-a212-45ab-83d4-287591ef97ab>.

Machold et al.; "Sonic Hedgehog Is Required for Progenitor Cell Maintenance in Telencephalic Stem Cell Niches;" Neuron., vol. 39, No. 6; pp. 937-950; dated Sep. 2003; retrieved on May 9, 2014 from <http://www.sciencedirect.com/science/article/pii/S0896627303005610/pdfft?md5=229c1da05dbe3cc6d4f285d016ad3ccf&pid=1-s2.0-S0896627303005610-main.pdf>.

Mahindroo et al.; "Hedgehog-Gli Signaling Pathway Inhibitors as Anticancer Agents;" J. Med. Chem., vol. 52, No. 13; p. 3829-3845; dated Jul. 2009; abstract retrieved on May 9, 2014 from <http://pubs.acs.org/doi/abs/10.1021/jm801420y>.

Marti et al.; "Sonic hedgehog in CNS development: one signal, multiple outputs;" Trends Neurosci., vol. 25, No. 2; pp. 89-96; dated Feb. 2002; abstract retrieved on May 9, 2014 from <http://www.cell.com/trends/neurosciences/abstract/S0166-2236(02)02062-3>.

Mastronardi et al.; "Attenuation of Experimental Autoimmune Encephalomyelitis and Nonimmune Demyelination by IFN-β plus Vitamin B12: Treatment to Modify Notch-1/Sonic Hedgehog Balance;" J. Immunol., vol. 172, No. 10; pp. 6418-6426; dated May 2004; retrieved on May 9, 2014 from <http://www.jimmunol.org/content/172/10/6418.full.pdf+html>.

Ng et al.; "The Hedgehog's tale: developing strategies for targeting cancer;" Nature Review Cancer, No. 11, No. 7; pp. 493-501 dated May 2011; abstract retrieved on May 9, 2014 from <http://www.nature.com/nrc/journal/v11/n7/abs/nrc3079.html>.

Pan et al.; "Discovery of NVP-LDE225, a Potent and Selective Smoothened Antagonist;" ACS Med. Chem. Lett., vol. 1, No. 3; pp. 130-134; dated Jun. 2010; retrieved from <https://www.researchgate.net/publication/231711984_Discovery_of_NVP-LDE225_a_Potent_and_Selective_Smoothened_Antagonist>.

Pepinsky et al.; "Identification of a Palmitic Acid-modified Form of Human Sonic hedgehog;" J. Biol. Chem., vol. 273, No. 22; p. 14037-14045; dated May 1998; retrieved on May 9, 2014 from <http://www.jbc.org/content/273/22/14037.full.pdf+html>.

Peukert et al.; "Small-Molecule Inhibitors of the Hedgehog Signaling Pathway as Cancer Therapeutics;" ChemMedChem, vol. 5, No. 4; pp. 500-512; dated Apr. 2010; retrieved on May 9, 2014 from <http://onlinelibrary.wiley.com/doi/10.1002/cmdc.201000011/pdf>.

Pourshafie, M. R., et al.; "Binding interactions of *Escherichia coli* with globotetraosylceramide (globoside) using a surface plasmon resonance biosensor;" J. Microbiol. Meth., vol. 58, No. 3; pp. 313-320; dated Sep. 2004; abstract retrieved on May 9, 2014 from <http://www.sciencedirect.com/science/article/pii/S0167701204001150>.

Rivoyre et al.; "Human receptor Smoothened, a mediator of Hedgehog signalling, expressed in its native conformation in yeast.;" FEBS Letters, vol. 579, No. 6; pp. 1529-1533; dated Feb. 2005; retrieved on May 9, 2014 from <http://www.sciencedirect.com/science/article/pii/S0014579305001559/pdfft?md5=14719c55acb4a406c2fcd417t137b5cea&pid=1-s2.0-S0014579305001559-main.pdf>.

Robarge et al.; "Design and Synthesis of [(2,3-Dichlorophenyl)piperazin-1-yl]alkylfluorenylcarboxamides as Novel Ligands Selective for the Dopamine D3 Receptor Subtype;"J. Med. Chem., vol. 44, No. 19; p. 3175-3186; dated Sep. 2001; abstract retrieved on May 9, 2014 from <http://pubs.acs.org/doi/abs/10.1021/jm010146o>.

Rohatgi et al.; "Hedgehog signal transduction by Smoothened: Pharmacologic evidence for a 2-step activation process;" Proc. Natl. Acad. Sci., vol. 106, No. 9; pp. 3196-3201; dated Mar. 2009; retrieved on May 9, 2014 from <http://www.pnas.org/content/106/9/3196.full.pdf+html>.

Rominger et al.; "Evidence for Allosteric Interactions of Antagonist Binding to the Smoothened Receptor;" JPET, vol. 329, No. 3; pp. 995-1005; dated Mar. 2009; retrieved on May 9, 2014 from <http://jpet.aspetjournals.org/content/329/3/995.full.pdf+html>.

Roudaut et al.; "Identification and Mechanism of Action of the Acylguanidine MRT-83, a Novel Potent Smoothened Antagonist;" Mol. Pharrnacol., vol. 79, No. 2; pp. 453-460; dated Mar. 2011; retrieved on May 9, 2014 from <http://molpharm.aspetjournals.org/content/79/3/453.full.pdf+html>.

Scales et al; "Mechanisms of Hedgehog pathway activation in cancer and implications for therapy;" Trends Pharmacol. Sci., vol. 30, No. 6; pp. 303-312; dated Jun. 2009; abstract retrieved on May 12, 214 from <http://www.cell.com/trends/pharmacological-sciences/abstract/S0165-6147(09)00069-8>.

(56) References Cited

OTHER PUBLICATIONS

Solinas, A., et al.; "Acylthiourea, Acylurea, and Acylguanidine Derivatives with Potent Hedgehog Inhibiting Activity;" J. Med. Chem., vol. 55, No. 4; pp. 1559-1571; dated Feb. 2012.

Solorzano et al.; "Synthesis and Structure—Activity Relationships of N-(2-Oxo-3-oxetanyl)amides as N-Acylethanolamine-hydrolyzing Acid Amidase Inhibitors;" J. Med. Chem., vol. 53, No. 15; p. 5770-5781; dated Aug. 2010; abstract retrieved on May 9, 2014 from <http://pubs.acs.org/doi/abs/10.1021/jm100582w>.

Taipale et al.; "Effects of oncogenic mutations in Smoothened and Patched can be reversed by cyclopamine;" Nature, vol. 406, No. 6799; pp. 1005-1009; dated Aug. 2000; retrieved on May 12, 2014 from <https://www.researchgate.net/publication/232774788_Effects_of_oncogenic_mutations_in_Smoothened_and_Patchedcan_be_reversed_by_cyclopamine>.

Traiffort et al.; "Functional Characterization of Sonic Hedgehog Mutations Associated with Holoprosencephaly;" J. Biol. Chem., vol. 279, No. 41; pp. 42889-42997; dated Oct. 2004; retrieved on May 9, 2014 from <http://www.jbc.org/content/279/41/42889.full.pdf+html>.

Traiffort et al.; "Sonic Hedgehog signaling in the mammalian brain;" J. Neurochem., vol. 113, No. 3; pp. 576-590; dated May 2010; retrieved on May 12, 2014 from <http://onlinelibrary.wiley.com/doi/10.1111/j.1471-4159.2010.06642.x/pdf>.

Tremblay et al.; "Discovery of a Potent and Orally Active Hedgehog Pathway Antagonist (IPI-926);" J. Med. Chem., vol. 52, No. 14; pp. 4400-4418; dated Jul. 2009; abstract retrieved on May 9, 2014 from <http://pubs.acs.org/doi/abs/10.1021/jm900305z>.

Tsuboi et al.; "Intrastriatal Injection of Sonic Hedgehog Reduces Behavioral Impairment in a Rat Model of Parkinson's Disease;" Exp. Neurol., vol. 173, No. 1; pp. 95-104; dated Jan. 2002; abstract retrieved on May 12, 2014 from <http://www.sciencedirect.com/science/article/pii/S0014488601978252>.

Tsukamoto et al.; "Palladium(0)-catalyzed direct cross-coupling reaction of allylic alcohols with aryl- and alkenylboronic acids;" Org. Biomol. Chem., vol. 6, No. 16; P. 3005-3013; dated 2008; abstract retrieved on May 9, 2014 from <http://pubs.rsc.org/en/content/articlelanding/2008/ob/b804991b#!divAbstract>.

Weschler-Reya er al.; "The Developmental Biology of Brain Tumors;" Annu. Rev. Neurosci., vol. 24; pp. 385-428; dated Mar. 2001; retrieved on May 12, 2014 from <http://www.wechsler-reya.org/manage/user_files/89-1142711085.pdf>.

Wikstrom, A., et al.; "Probing the interaction of coagulation factors with phospholipid vesicle surfaces by surface plasma resonance;" Anal. Biochem., vol. 362, No. 1; pp. 98-107; dated Mar. 2007; abstract retrieved on May 12, 2014 from <http://www.sciencedirect.corn/science/article/pii/S0003269706008864>.

Wu et al.; "Purmorphamine Induces Osteogenesis by Activation of the Hedgehog Signaling Pathway;" Chemistry & Biology, vol. 11, No. 9; pp. 1229-1238; dated Sep. 2004; retrieved on May 12, 2014 from <http://www.cell.com/chemistry-biology/pdf/S1074-5521(04)00221-2.pdf>.

Yang et al.; The Journal of Biological Chemistry; dated Apr. 14, 2009.

Yauch et al.; "A paracrine requirement for hedgehog signalling in cancer;" Nature, vol. 455, No. 7211; pp. 406-410; dated Sep. 2008; retrieved on May 12, 2009 from <https://www.researchgate.net/publication/23220431_A_paracrine_requirement_for_hedgehog_signalling_in_cancer>.

Yauch et al.; "Smoothened Mutation Confers Resistance to a Hedgehog Pathway Inhibitor in Medulloblastoma;" Science, vol. 326, No. 5952; pp. 572-574; dated Oct. 2009; retrieved on May 12, 2014 from <https://www.researchgate.net/publication/26786112_Smoothened_mutation_confers_resistance_to_a_Hedgehog_pathway_inhibitor_in_medulloblastoma>.

Zhang et al.; "Palladium-Iminodiacetic Acid Immobilized on pH-Responsive Polymeric Microspheres: Efficient Quasi-Homogeneous Catalyst for Suzuki and Heck Reactions in Aqueous Solution;" Adv. Cat. Synth., vol. 350, No. 13; p. 2065-2076; dated Sep. 2008; abstract retrieved on May 9, 2014 from <http://onlinelibrary.wiley.com/doi/10.1002/adsc.200800304/abstract>.

International Preliminary Report on Patentability for Application No. PCT/IB2012/055033; dated Mar. 25, 2014.

International Search Report and Written Opinion for Application No. PCT/IB2012/055033; dated Nov. 30, 2012.

Yang, Hongbo et al.; "Converse Conformational Control of Smoothened Activity by Structurally Related Small Molecules"; The Journal of Biological Chemistry, vol. 284, No. 31, pp. 20876/20884; Jul. 31, 2009.

* cited by examiner

COMPOUNDS MODULATING THE HEDGEHOG PROTEIN SIGNALING PATHWAY, MARKED FORMS THEREOF, AND APPLICATIONS

This application is a 371 of PCT/IB2012/055033, filed Sep. 21, 2012.

FIELD

The present invention relates to novel compounds of formula (I), use thereof as medication, notably for treating tumors associated with hyperactivation of the Hedgehog protein signalling pathway, for treating disorders of the neurodegenerative type, for treating diseases connected with cerebral development (holoprosencephaly), to the control of stem cells, to the treatment of cerebrovascular accidents and to cardiovascular accidents, as well as to diseases of oligodendrocytes and Schwann cells, for application thereof in vitro for modulating the renewal of human or animal stem cells, as well as for treating diabetes. The present invention also relates to pharmaceutical compositions comprising at least one compound of formula (I), as active principle. A method of radiolabeling of compounds of formula (I), the labeled compounds and use thereof as research tools also form part of the invention. Finally, the present invention also relates to a method of screening and/or identifying ligands of the Smo binding sites of the Smoothened receptor, methods of identifying agonists and antagonists of the Smoothened receptor and a method of identifying cells, such as tumor cells expressing the Smoothened receptor.

BACKGROUND

The Hedgehog signalling molecule (Hh) is a secreted autoproteolytic protein that activates the Hedgehog protein signalling pathway, which is a signalling pathway that plays a fundamental role in the morphogenesis of numerous tissues, in particular in the formation of the endoderm and of the embryonic axis, development of the brain and of the hair follicles, as well as in cellular proliferation, and is thought to be involved in tissue maintenance and repair in adults (Ingham et al., Genes Dev., 2001, 15, 3059-3087; Marti et al., Trends Neurosci., 2002, 25, 89-96; Weschler et al., Annu. Rev. Neurosci., 2001, 24, 385-428).

The Hedgehog protein and the associated transduction pathway, initially demonstrated in Drosophila, are conserved in vertebrates and invertebrates. A single homolog of Hh is present in Drosophila, whereas three homologs of Hh: Sonic (Shh), Indian (Ihh) and Desert (Dhh) are present in mammals. Among these three homologs, Shh has received most study owing to its extended expression profile during development. Shh participates in ventralization of the neural tube, specifying the early phenotype of several neuronal types along the ventral midline (motoneurons of the spinal cord, dopaminergic or cholinergic neurons), and inducing the generation of the oligodendrocyte precursors starting from the ventral spinal cord. Moreover, Shh induces survival of the GABAergic and dopaminergic neurons, orients the future of the serotoninergic precursors and prevents death of dopaminergic neurons caused by the toxin MPP. Finally it induces proliferation of the granule cell precursors in the early postnatal cerebellum. As for the other members of the Hedgehog family, they participate in the development of bone tissue (Ihh), of the testes and of the peripheral nerves (Dhh), respectively. Moreover, the results obtained with Shh also apply to Dhh and Ihh.

Shh is synthesized in the form of a precursor that undergoes a series of post-translational modifications during which the protein is cleaved by an enzyme activity present in its C-terminal portion. This autoproteolysis generates a C-terminal fragment (ShhC) and an N-terminal fragment (ShhN) that represents the active fragment. During this reaction, addition of a cholesterol molecule in the C-terminal portion of ShhN is also observed, which promotes anchorage of ShhN to the membrane. Finally an acetyl transferase allows addition of a palmitate molecule on a cysteine residue near the N-terminal end. These events produce a biologically active Shh protein. Secretion of the protein is dependent on the protein Dispatched (Disp), two isoforms of which, Disp 1 and 2, exist in mammals (Heretsch et al., 2010, Bioorg. Med. Chem. Lett. 18: 6613-6624).

The soluble ShhN fragment transmits its action via a complex containing two transmembrane proteins: Patched (Ptc), a protein with 12 transmembrane domains having a structure of the transporter type, and Smoothened (Smo), a protein with 7 transmembrane domains homologous to the members of the superfamily of receptors coupled to proteins G (RCPG). In mammals, there is a second form of Patched: Ptc2.

In the absence of its ligand Shh, Ptc inhibits Smo. An intracellular cascade, involving a great many factors including the protein Suppressor of Fused (SuFu) and the protein PKA, is then induced. SuFu is a negative regulator of the Shh signalling pathway, it can bind to the three transcription factors of the Gli family and regulate their activation. Moreover, deletion of Sufu results in activation of the pathway. The transcription factors of the Gli family are then phosphorylated, ubiquitinylated and then cleaved in their negative form (GliR) by the proteasome, GliR penetrates into the nucleus and transcription is inactive. When Shh binds to Ptc, the inhibition that the latter exerts on Smo is raised with nuclear translocation of the active form of the Gli transcription factors (GliA) and transcriptional activation of target genes such as ptc and gli1.

The protein Hedgehog interacting protein (Hip) is capable of binding Shh with an affinity comparable to that of the protein Ptc (Traiffort et al., J. Neurochem., 2010, 113: 576-590). Hip is regarded as a negative modulator of the pathway because by binding Shh it decreases the amount of ligand available for activating the signalling pathway via Ptc. Cdo and Boc belong to the family of cell surface proteins possessing immunoglobulin and fibronectin motifs of type III. These proteins regulate the Shh signalling pathway positively by facilitating presentation of the ligand Shh to Ptc, by increasing the amounts of morphogen in the vicinity of the target cells and possibly by affecting the activity of the Gli proteins (Heretsch et al., 2010, Bioorg. Med. Chem. Lett 18: 6613-24: Scales and de Sauvage, 2009, Trends Pharmacol. Sci. 30: 303-312).

The regulatory role of the Hedgehog protein signalling pathway during embryonic development has been studied extensively: Hh has been associated with the processes of maintenance and repair of normal tissue, with spatiotemporal regulation of proliferation and differentiation, thus allowing developing tissues to reach their correct size with the appropriate cell types and appropriate degrees of vascularization and innervation. It has notably been implicated in the development of the central nervous system (Dessaud et al., 2008, Development, 135: 2489-503). The essential role of the Hh signalling function is demonstrated by the dramatic consequences of defects in this signalling pathway in the human fetus, such as holoprosencephaly observed with mutants of Shh (Traiffort et al., J. Biol. Chem., 2004, 279: 42889-42997).

More recently the Shh pathway was identified in the adult brain, where the amino-terminal active form of the molecule is expressed in a great many regions of the mature nervous system suggesting new roles for this pathway. In fact, it notably participates in establishment and maintenance of neurogenic niches and regulates the proliferation of neural or glial precursors in the adult brain (Traiffort et al., 2010, J. Neurochem., 113: 576-590). Modulation of the Shh signalling pathway therefore represents a challenge for the development of therapies for neurodegenerative diseases. Studies have already demonstrated positive effects of activation of the Shh signalling pathway by the Shh protein itself, on reduction of behavioral disorders in rats with Parkinson's disease (Tsuboi et al., 2002, Exp. Neurol. 173: 95-104) or on remyelinization of neurons in rats with multiple sclerosis (Mastronardi et al. 2004, J. Immunol. 172: 6418-26). Moreover, it has been shown that activation of the Shh signalling pathway by a Smo agonist allows an increase in proliferation of neural precursors at the level of areas of neurogenesis in the adult mouse (Machold et al., 2003, Neuron., 39: 937-950). However, the Smo agonists remain few in number and are still poorly characterized.

Dysfunctions of the Shh signalling pathway have also been associated with many cancers. In fact, mutations that inactivate Ptc are associated with Gorlin syndrome or basal cell nevus syndrome, an autosomal dominant disease characterized by craniofacial and cerebral malformations, but especially by a high incidence of various tumors, more particularly of basal cell carcinomas at the cutaneous level and medulloblastomas, at the cerebellum level. Mutations of the human genes Ptc or Smo are also observed in primary neuroectodermal tumors of the central nervous system, principally medulloblastomas (30% of cases), but also in sporadic forms of basal cell carcinomas (40% and 20% of cases for Ptc and Smo respectively). Moreover, mutations of Shh are also associated with basal cell carcinomas. Other types of tumors have also been associated with a defect of the Hedgehog signalling pathway, and the localization of these tumors is closely correlated with the expression sites of the components of the pathway during embryonic development (Scales and de Sauvage, 2009, Trends in Pharmacol. Sci., 30: 303-312). We may mention, as nonlimiting examples: breast cancers and meningiomas associated with mutations of Ptc, glioblastomas associated with mutations of Gli, gastrointestinal cancers, notably primary cancers of the stomach and colon, cancers of the prostate and of the bladder, fibromas and dermoid cysts of the ovary, rhabdomyosarcomas, small cell lung cancers, squamous cell oral carcinomas.

Owing to the crucial role of the Hedgehog protein signalling pathway in numerous physiological and pathological processes, the components of this pathway, such as the proteins Smoothened (Smo 1 and Smo 2), Frizzled (Fz 1 to Fz 10), Patched (Ptc 1 and Ptc 2), the proteins Dispatched (Disp 1 and Disp 2) or also the protein Hip represent targets for the development of new molecules capable of modulating (activating or inhibiting) this pathway and therefore of regulating development positively or negatively [proliferation, differentiation, migration, survival (apoptosis)] and/or the activity of differentiated cells and of stem cells, in vitro and/or in vivo in the embryo or in the adult.

It has been demonstrated that such molecules are useful in the treatment of tumors associated with hyperactivation of the Hedgehog pathway (Scales and de Sauvage, 2009, Trends in Pharmacol. Sci., 30: 303-312). Such molecules might therefore be usable in the treatment of various tumors such as nerve tissue tumors (medulloblastomas, primary neuroectodermal tumors, glioblastomas, meningiomas and oligodendroglio-mas), skin tumors (basal cell carcinomas, trichoepitheliomas), tumors of muscle and bone tissues (rhabdomyosarcomas, osteosarcomas, melanomas) and tumors of other tissues (kidney, bladder, prostate, lung, stomach, pancreas, breast, liver).

Such molecules are also useful in the treatment of disorders of the neurodegenerative type requiring blocking of the Hedgehog pathway (Parkinson's disease, Huntington's chorea, Alzheimer's disease, multiple sclerosis, motor neuron disease), and diseases in which blocking of the Hedgehog signalling pathway might be beneficial, such as diabetes.

Such molecules are also useful in medical or surgical treatment (plastic or reconstructive surgery, grafts of tissues or of organs) of numerous acute, subacute or chronic, genetic or acquired disorders—involving a tissue dysfunction connected with deregulation of the Hedgehog pathway—for inducing the formation, regeneration, repair and/or increase in activity of tissues such as nervous tissue [central nervous system (brain) and peripheral nervous system (sensory, motor, sympathetic neurons)], bone, cartilage, testes, liver, spleen, intestine, pancreas, kidneys, smooth and skeletal muscles, heart, lungs, skin and hair, mucosae, blood cells and cells of the immune system. As nonlimiting examples of these disorders, we may notably mention neuropathies and the associated neuromuscular diseases, diabetes, alopecia, burns, ulcerations (skin and mucosae) and disorders of spermatogenesis.

Various molecules capable of modulating the activity of the Hedgehog pathway have been identified.

Firstly, the Hedgehog proteins and derived polypeptides (fragments, variants etc.), notably agonists and antagonists of the Hedgehog proteins (International Application PCT WO 01/98344 in the name of BIOGEN); owing to their size, these proteins and the derived polypeptides cannot cross the blood-brain barrier and therefore cannot be administered systemically, notably for treating brain tumors connected with hyperactivation of the Hedgehog protein signalling pathway. Moreover, such molecules are of low stability, and are difficult to produce and purify. Conversely, molecules exist that inhibit the effect of the Shh ligand, robotnikinin and the 5E1 monoclonal antibody.

The Hh signalling pathway can also be modulated further downstream. The inhibitory effect of Ptc on Smo can be modulated, for example. It is increased by statins and reduced by oxysterols by a mechanism that is not yet properly understood (Heretsch et al., Bioorg. Med. Chem. Lett., 2010, 18: 6613-6624). Natural products (Physalin F) or synthetic products (GANT58, GANT61, HPI-1) are also known to inhibit the binding of the Gli transcription factors to the DNA in the nucleus.

However, most research is focused on the discovery of modulators acting at the level of the Smoothened receptor:
  heterocyclic organic molecules inhibiting or activating (SAG and derivatives) the Hh signalling pathway: International Application PCT WO 01/74344 in the name of CURIS; Chen et al., PNAS, 2002, 99, 14071-14076,
  purmorphamine, a small molecule activating the Hh signalling pathway: Wu et al., Chemistry & Biology, 2004, 1229-1238,
  nitrogen-containing heterocyclic molecules: International Applications PCT WO 01/19800, WO 01/26644 and WO 02/30421 in the name of CURIS; Kamenetsky et al., J. Biol., 2002, 1, 1-19,
  plant steroids derived from *Veratrum* spp. (jervine, cyclopamine and cycloposine) and from *Solanum* spp. (solanidine), substituted in position 16, 17 or 18 with an amine or an amine derivative, and cholesterol: U.S. Pat.

No. 6,432,970 and International Applications PCT WO 99/52534 and WO 01/27135 in the name of JOHNS HOPKINS UNIVERSITY SCHOOL OF MEDICINE; U.S. Pat. No. 6,291,516; International Application PCT WO 00/41545 in the name of ONTOGENY INC.; International Application PCT WO 02/30462 in the name of CURIS; Taipale et al., Nature, 2000, 406, 1005-1009; Berman et al., Science, 2002, 297, 1559-1561. However, it was demonstrated that concentrations of cyclopamine above 10 µM proved to be cytotoxic for the cells (Borzillo et al., Curr. Top Med. Chem., 2005, 5(2), 147-157). Moreover, the effects in vivo of cyclopamine on tumor growth have been called into question as they might be connected with an activity outside of the tumor itself (Yauch et al., 2008, Nature, 455: 406-410). A derivative of cyclopamine (IPI-926) is currently in clinical phase II (Mahindroo et al., J. Med. Chem., 2009, 52, 3829; Tremblay et al., J. Med. Chem., 2009, 52: 14, 4400-4418), mifepristone (17β-hydroxy 11β-(4-dimethylamino phenyl) 17α-(prop-1-ynyl)estra-4,9-dien-3-one), also called RU-486 or RU-38486 (French patent FR 2 850 022 in the name of the CNRS) for which an inhibitory activity on the activity of the Hedgehog protein signalling pathway has been demonstrated, the molecules SANT74 and SANT75 having a structure similar to that of SAG, synthetic activating compound of the chlorobenzothiophene type (CAS No.: 364590-63-6) are also known to be stable inhibitors for effectively controlling the conformation of the activator Smo (Yang et al., The Journal of Biological Chemistry, published Apr. 14, 2009).

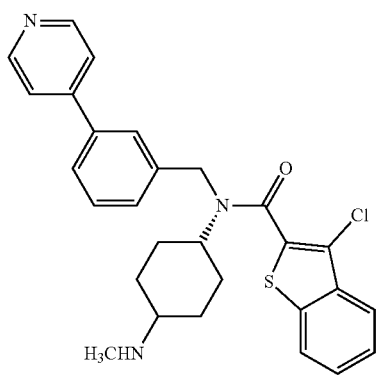

SANT75

More recently, other compounds that inhibit the Hedgehog signalling pathway have also been described (Peukert and Miller-Moslin, 2010, ChemMedChem 5: 500-512; Low and De Sauvage, 2010, J. Clin. Oncol.; Ng and Curran, 2011, Nature Review Cancer):

Inhibitors based on bisamide (International Application PCT WO 2007/059157 in the name of GENENTECH INC. and CURIS INC.) and on pyridyl (International Application PCT WO 2006/028958 in the name of GENENTECH INC. and CURIS INC; US Patent 2009/0281089 in the name of GENENTECH INC.). One of the pyridyl-based compounds, GDC-0449 (clinical phase II) has shown its efficacy in a patient with medulloblastoma metastases. However, the patient gradually developed resistance to the molecule. A mutation of an aspartic acid (D473H) of Smo appeared. This interferes with the compound's ability to bind to Smo and inhibit this pathway. A mutation of the same amino acid was identified in a mouse model with medulloblastomas, treated with this compound (Yauch et al., 2009, Science 326: 572-574).

Inhibitors developed by the company Novartis. For example, LDE225 (clinical phase II) has been tested for treating medulloblastomas in the mouse model and has induced regression of these tumors. However, resistance was observed over the course of the treatment. A study has revealed several mechanisms of resistance including chromosomal amplification of Gli2 and, more rarely, point mutations of the Smo receptor that lead to reactivation of tumor growth. Positive regulation of phosphatidylinositol 3-kinase (PI3K) signalling has also been identified (Buonamici et al., 2010, Sci. Transl. Med., 51-70).

Inhibitors developed by Bristol-Myers Squibb Inc. such as BMS-833923 (XL-139).

Inhibitors described by the company Pfizer Products, Inc. (WO 2008/075196 and US 2009/0005416). PF-04449913 is currently in clinical phase II.

Inhibitors described by the company MERCK (Dessole et al., 2009, Bioorg. & Med. Chem. Lett. 19: 4191-4195).

The compounds LEQ506 of Novartis and TAK-441 of the company Millennium have also just entered clinical phase I.

Inhibitors based on acyl-ureas, -thioureas and -guanidines have also been protected as modulators of the Hedgehog pathway (WO 2009/130422 and WO 2011/010013 in the name of the CNRS). The latter have the advantage of being easy to prepare in comparison with the other existing molecules. Moreover, the acyl-guanidine derivatives are water-soluble.

SUMMARY

The inventors now set themselves the aim of providing novel compounds that are modulators (stimulators or inhibitors) of the Hedgehog protein signalling pathway that respond better to practical needs, notably in that they are simple to synthesize and potentially usable in human therapy.

This objective is achieved by the compounds of formula (I) that are described below and that constitute the first object of the invention, these compounds being the most powerful antagonists of the Smoothened receptor identified to date (5 to 30 times more powerful than the compounds currently in the clinical phase). These molecules also exhibit an affinity 10 to 30 times greater than that of the molecules GDC-0449 and LDE225, and moreover the latter have come up against the appearance of resistance in certain patients (resistances connected in particular with the appearance of mutations on the Smoothened receptor). Moreover, the molecules of the invention have the advantage of being prepared easily, generally in three or four steps, according to methods of synthesis similar to the conventional methods known by a person skilled in the art, the acyl-urea, -thiourea and guanidine compounds being easily accessible starting from available raw materials. The guanidine function, as base, is salifiable, which has the advantage of producing compounds having good solubility in an aqueous medium. All of the compounds of formula (I) are obtained very conveniently using simple chemical reactions that are well known by a person skilled in the art.

The present invention relates to the compounds of the following formula (I):

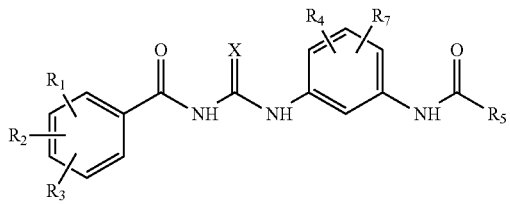

in which:
R₁, R₂ and R₃, which may be identical or different, independently of one another, represent a hydrogen or halogen atom, a hydroxyl radical, an alkyl, perfluoroalkyl, alkoxy, alkylthio or nitrile group, and said alkyl, perfluoroalkyl, alkoxy and alkylthio groups can comprise from 1 to 6 carbon atoms, X represents O, S or NH, and preferably X is NH, R₄ and R₇, which may be identical or different, independently of one another, represent a hydrogen or halogen atom or an alkyl group, R₅ represents one of the groups selected from:

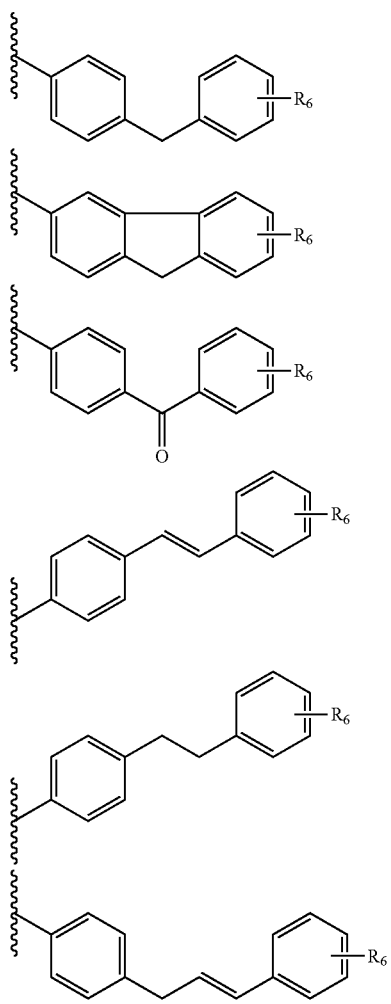

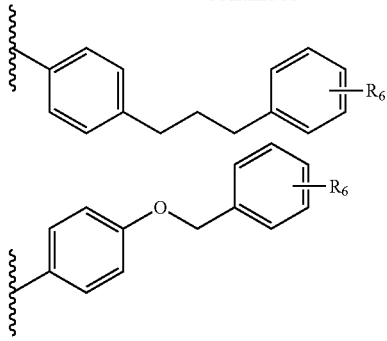

substituted with at least one radical R₆ representing a halogen atom or an alkyl, alkoxy, aminoalkyl, thioalkyl or hydroxyl group, and said alkyl, alkoxy, aminoalkyl and thioalkyl groups can comprise from 1 to 6 carbon atoms.

In the sense of the present invention, the terms have the following meanings:

Alkyl: a linear or branched saturated aliphatic hydrocarbon group, having from 1 to 6 carbon atoms, preferably from 1 to 2 carbon atoms. The term "branched" signifies that at least one lower alkyl group such as a methyl or an ethyl is carried by a linear alkyl chain. The term "lower" alkyl denotes an alkyl having 1 or 2 carbon atoms; the term "upper alkyl" denotes a linear or branched alkyl group having from 3 to 6 carbon atoms. As alkyl group, we may mention for example the methyl, ethyl, n-propyl, i-propyl, n-butyl, t-butyl and n-pentyl groups.

Halogen atom: denotes a bromine, chlorine, iodine or fluorine atom; the designations bromine, chlorine and fluorine being preferred;

Perfluoroalkyl: denotes an alkyl group as defined above in which all the hydrogen atoms have been replaced with fluorine atoms. Among the perfluoroalkyl groups, the trifluoromethyl and perfluoroethyl groups are preferred;

Alkoxy: denotes an O-alkyl group in which the alkyl group can have the same meaning as stated above. As examples of alkoxy groups, we may notably mention the methoxy, ethoxy, n-propoxy, isopropoxy, n-butoxy and pentoxy groups;

Alkylthio: denotes an alkyl-S group in which the alkyl group can have the same meaning as stated above. As examples of alkylthio group, we may notably mention the methylthio, ethylthio, isopropylthio, butylthio and pentylthio groups;

Aminoalkyl: denotes an alkyl-N group in which the alkyl group can have the same meaning as stated above. As examples of aminoalkyl group, we may notably mention the aminomethyl, aminoethyl, isopropylamino, butylamino and pentylamino groups.

According to a preferred embodiment of the invention, the compounds of formula (I) are selected from those in which R₁, R₂ and R₃ represent an alkoxy radical, and preferably a methoxy radical.

According to another preferred embodiment, R₄ and R₇ represent a hydrogen or chlorine atom, a methyl, ethyl or isopropyl group.

According to another advantageous embodiment, R₆ represents a halogen atom or an alkoxy or aminoalkyl group, and said alkoxy or aminoalkyl groups can comprise from 1 to 6 carbon atoms. More preferably, R₆ represents a chlorine or fluorine atom, a methoxy or dimethylamino radical.

As compounds of formula (I), we may mention in particular:

N—(N-(3-(4-benzoylbenzamido)-4-methylphenyl)carbamimidoyl)-3,4,5-trimethoxybenzamide hydrochloride of the following formula:

(Compound 7a)

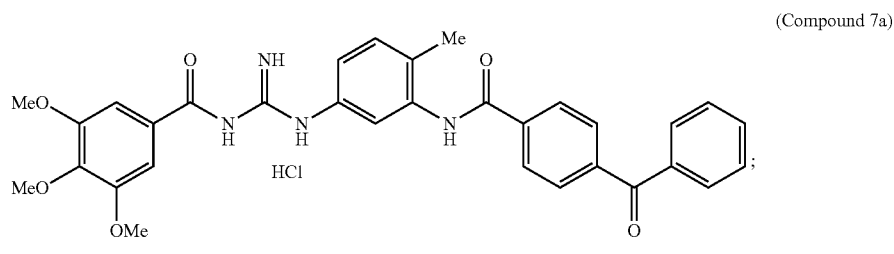

7a

N—(N-(3-(4-benzoylbenzamido)-4-methylphenyl)carbamimidoyl)-3,4,5-trimethoxybenzamide hydrochloride of the following formula:

(Compound 7b)

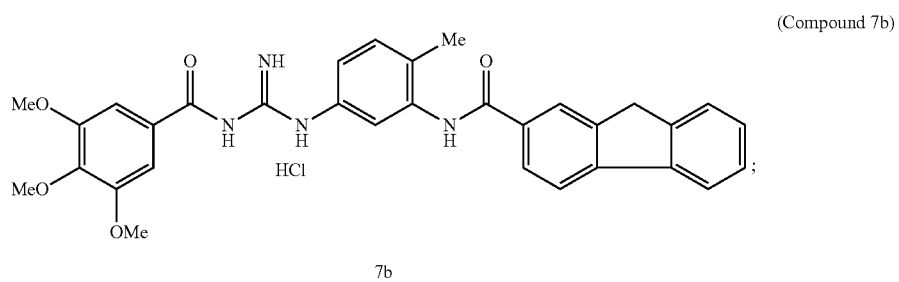 [SMILES: COc1cc(C(=O)NC(=N)Nc2ccc(C)c(NC(=O)c3ccc4c(c3)Cc3ccccc3-4)c2)cc(OC)c1OC ; Cl]

7b 3,4,5-trimethoxy-N—(N-(4-methyl-3-(4-(3-phenylpropyl)benzamido)phenyl)carbamimidoyl)benzamide hydrochloride of the following formula:

(Compound 7c)

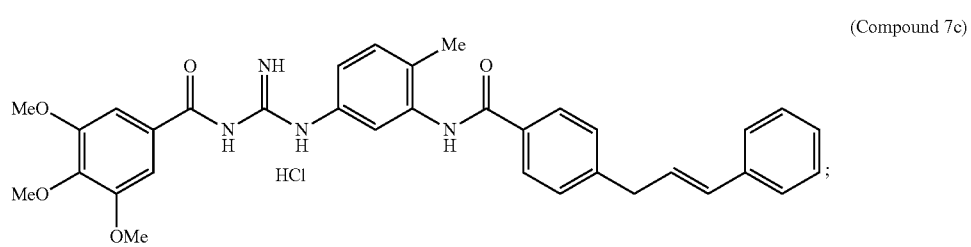

7c 3,4,5-trimethoxy-N—(N-(4-methyl-3-(4-phenethylbenzamido)phenyl)carbamimidoyl)benzamide hydrochloride of the following formula:

(Compound 7d)

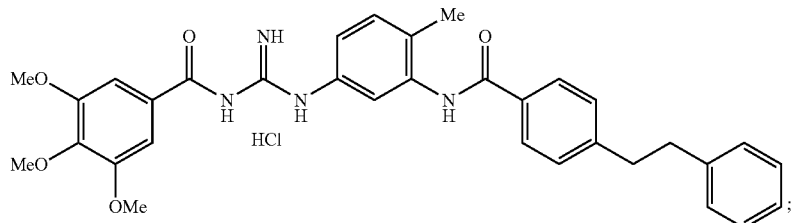

7d (E)-N—(N-(3-(4-cinnamylbenzamido)-4-methylphenyl)carbamimidoyl)-3,4,5-trimethoxybenzamide hydrochloride of the following formula:

(Compound 7e)

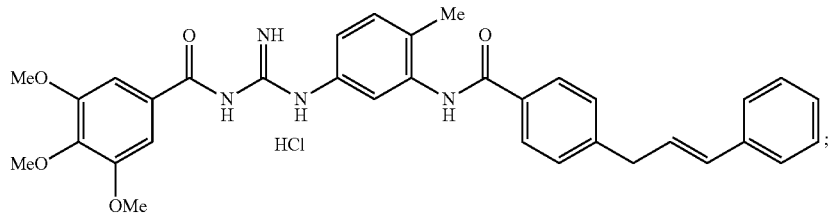

7e

N—(N-(3-(4-benzylbenzamido)-4-methylphenyl)carbamimidoyl)-3,4,5-trimethoxybenzamide hydrochloride of the following formula:

(Compound 7f)

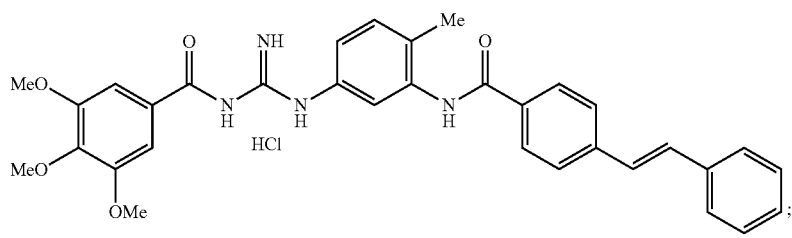

7f

N—(N-(3-(4-benzylbenzamido)-4-methylphenyl)carbamimidoyl)-3,4,5-trimethoxybenzamide hydrochloride of the following formula:

(Compound 7g)

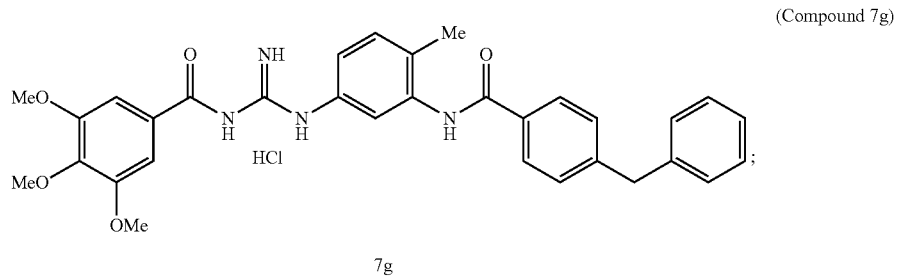 [SMILES: COc1cc(C(=O)NC(=N)Nc2ccc(C)c(NC(=O)c3ccc(Cc4ccccc4)cc3)c2)cc(OC)c1OC ; Cl]

7g

N—(N-(3-(4-(benzyloxy)benzamido)-4-methylphenyl)carbamimidoyl)-3,4,5-trimethoxybenzamide hydrochloride of the following formula:

(Compound 7h)

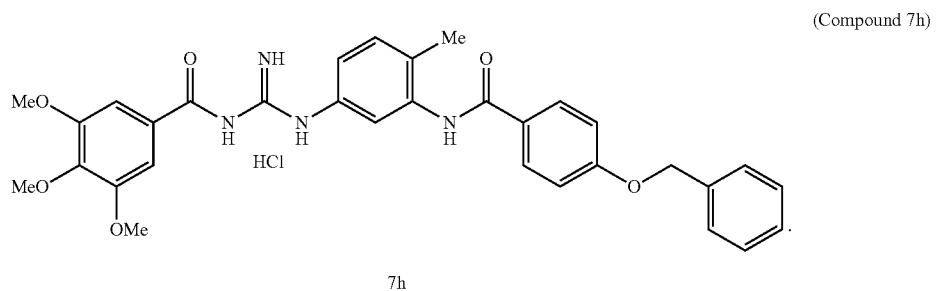 [SMILES: COc1cc(C(=O)NC(=N)Nc2ccc(C)c(NC(=O)c3ccc(OCc4ccccc4)cc3)c2)cc(OC)c1OC ; Cl]

7h

The compounds of formula (I) according to the invention can easily be prepared, generally in three or four steps, by methods of synthesis similar to the conventional methods known by a person skilled in the art.

Firstly a central fragment, fragment (VI), is prepared according to Scheme 1 above.

Scheme 1

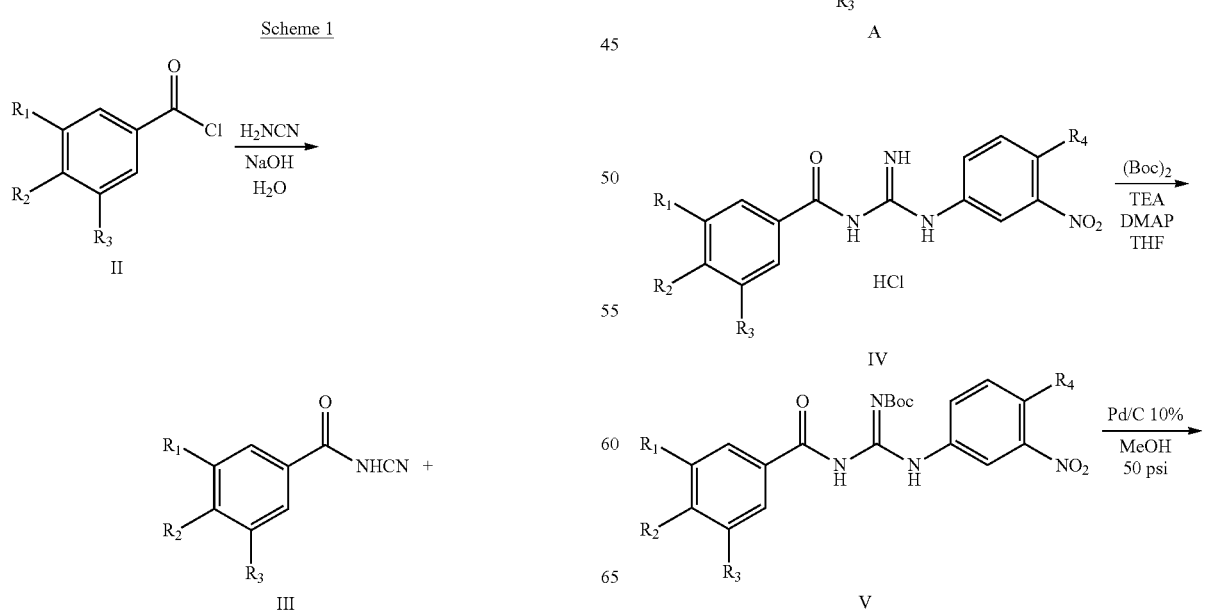

-continued

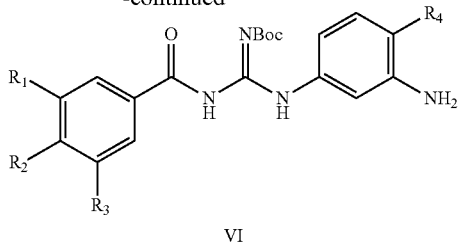

VI

It is a matter of condensing a benzoyl chloride (II) on the cyanamide in an aqueous medium, so as to obtain an acyl-cyanamide (III), which is in its turn condensed with an aniline (A) to obtain guanidine (IV).

The basic function of guanidine is then protected with a Boc residue in a basic medium, to obtain a nitro compound (V), and then reduced to amine by hydrogenation to obtain the intermediate aniline (VI).

Reaction scheme 2 below shows the preparation of compounds possessing groups $R_1=R_2=R_3=MeO$ in their formula (I).

The chlorides of acids (1a-h) are prepared as described in the literature (J. Med. Chem., 2001, 44, 3175; Chem. Eur. J. 2010, 16, 5848; Org. Lett. 2007, 9, 4571; Org. Biomol. Chem. 2008, 6, 3005; Adv. Cat. Synth. 2008, 350, 2065; J. Org. Chem. 2001, 66, 2874; J. Med. Chem. 2010, 53, 5770).

The intermediate (VI) is then condensed with various acid chlorides (1a-h), most often commercial, giving the expected compounds most often in the form of salts (hydrochlorides) (Scheme 2).

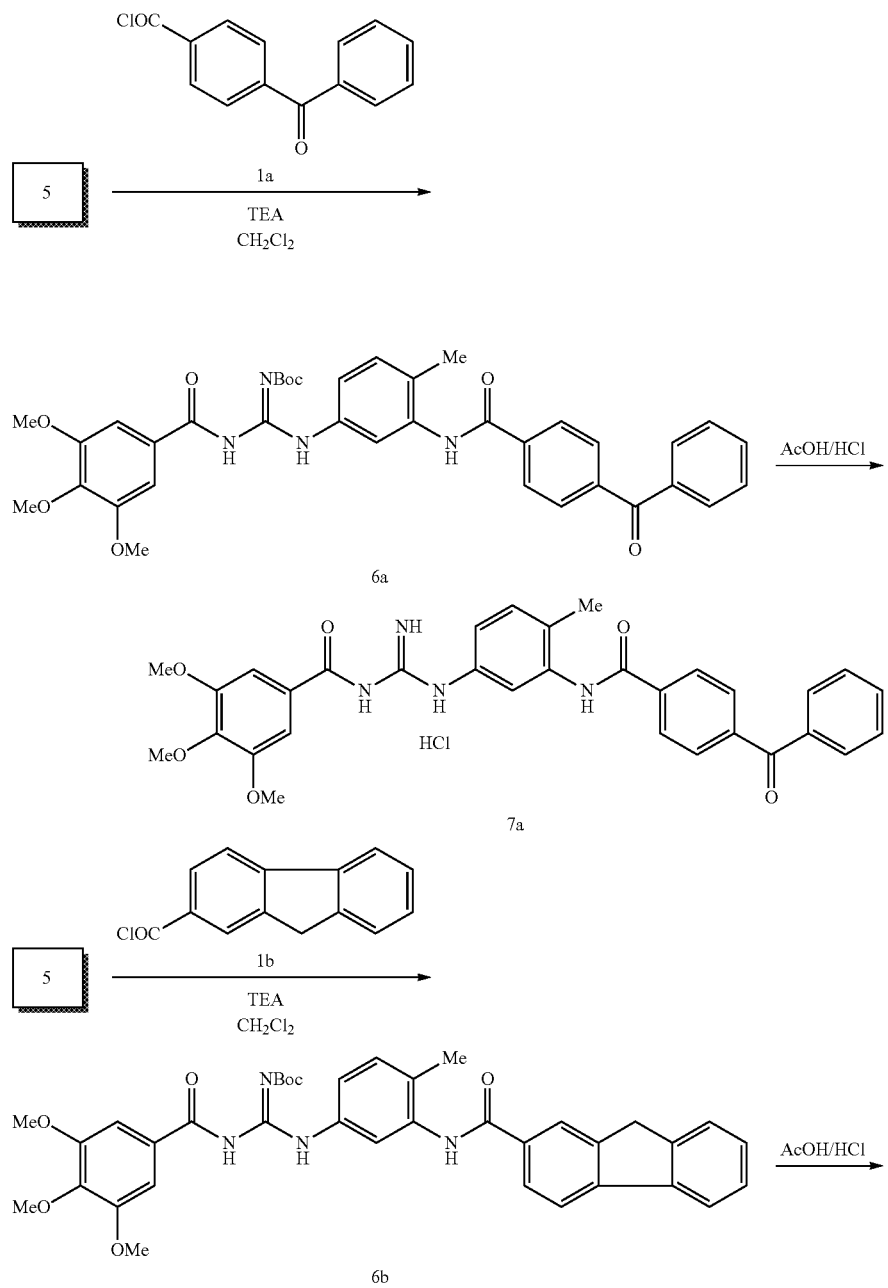

-continued
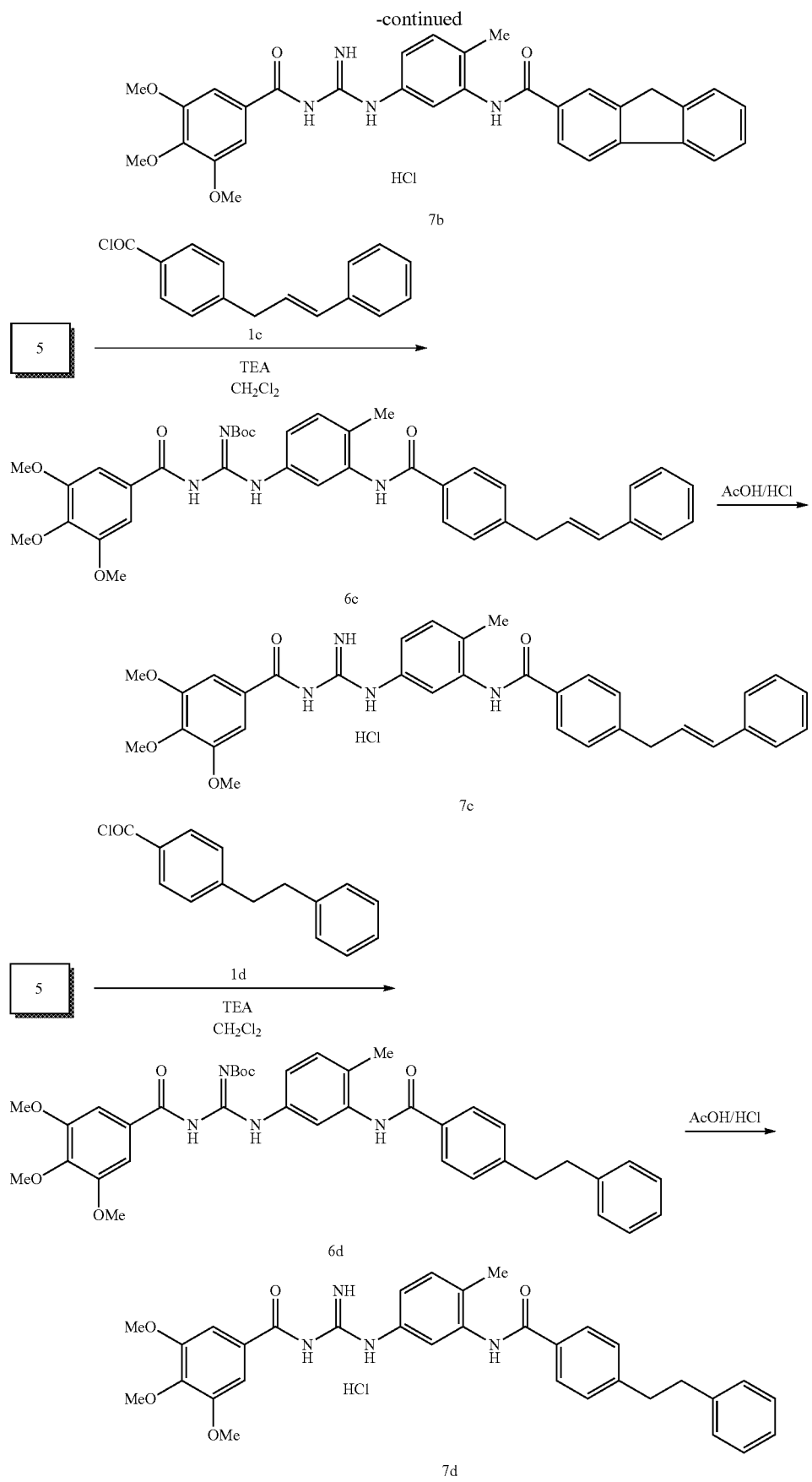

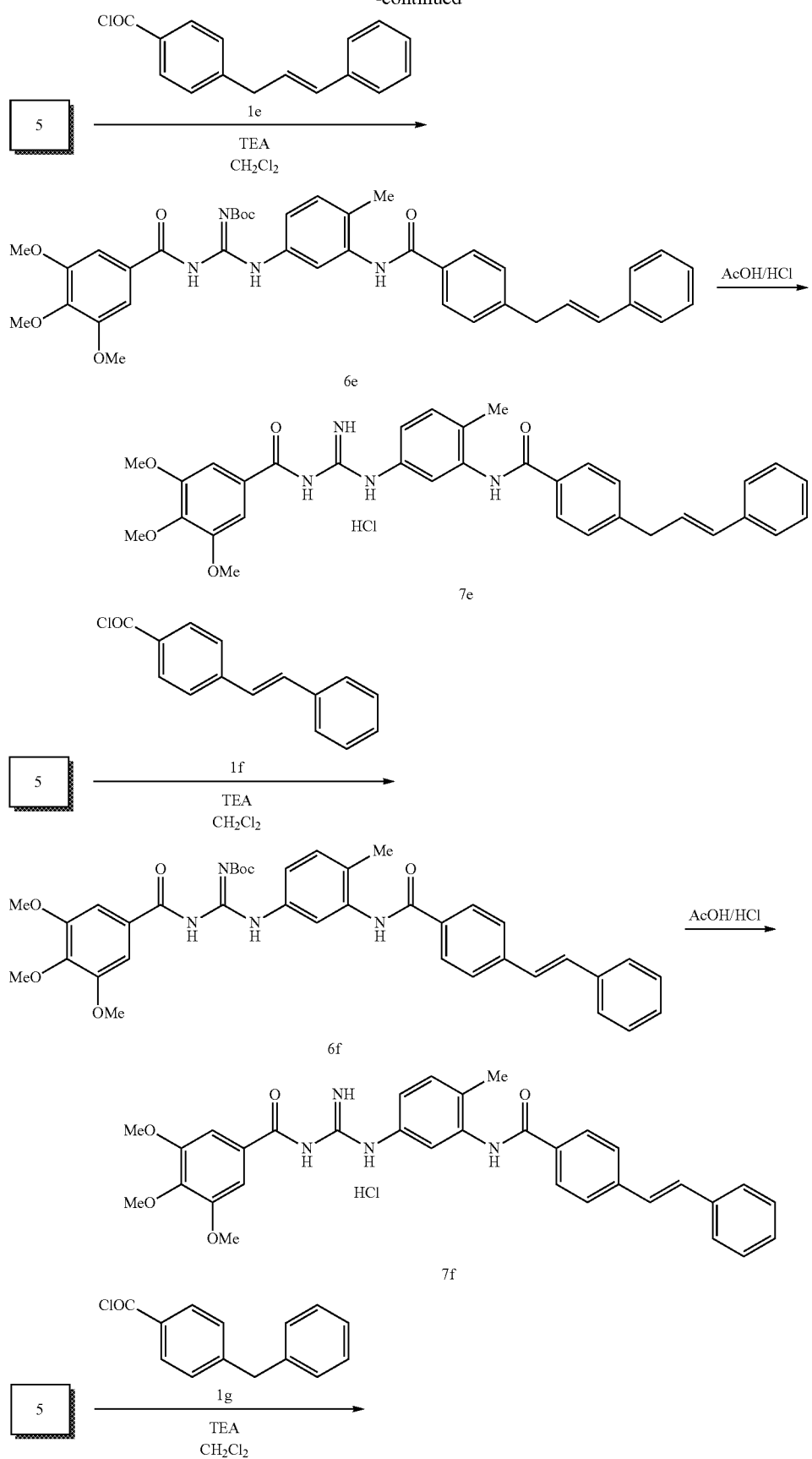

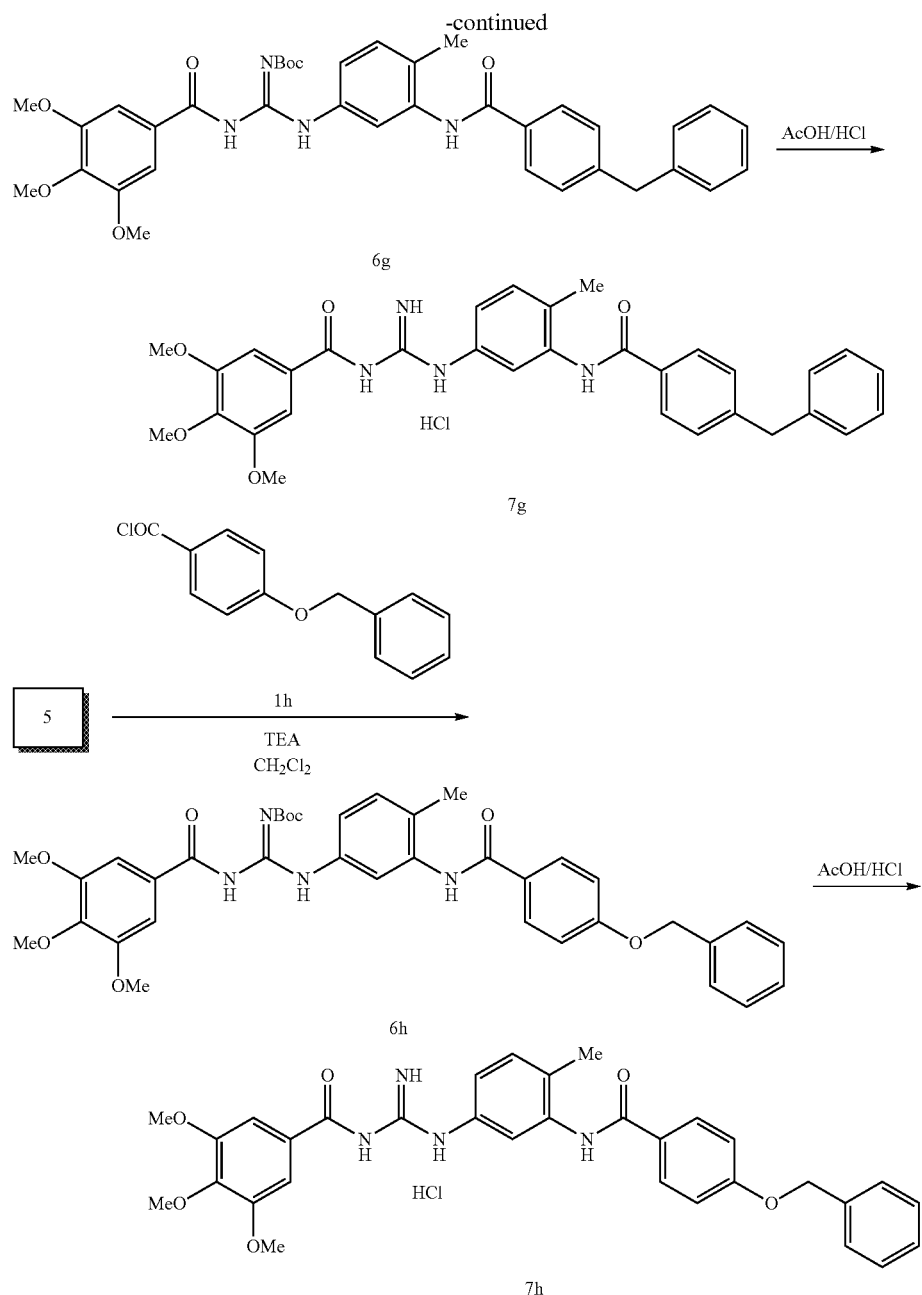

The compounds of formula (I) according to the invention have the property of modulating negatively (inhibitory effect) or positively (activating effect) the Hedgehog protein signalling pathway and can therefore be used as active principle for preparing a pharmaceutical composition intended for treatments of disorders associated with hyperactivation or deficit of the Hedgehog protein signalling pathway.

Consequently, the present invention also relates to the compounds of formula (I), for application thereof as medicinal product, and notably of the compounds of formula (I) for application thereof as medicinal product for treating tumors associated with hyperactivation of the Hedgehog protein signalling pathway.

More particularly, the present invention also relates to the compounds of formula (I):

- as medicinal product intended for treating tumors associated with hyperactivation of the Hedgehog protein signalling pathway; such tumors are notably nerve tissue tumors (medulloblastomas, neuroectodermal primary tumors, glioblastomas, meningiomas and oligodendrogliomas), skin tumors (basal cell carcinomas, trichoepitheliomas), tumors of muscle and bone tissues (rhabdomyosarcomas, osteosarcomas) or tumors of other tissues (kidney, bladder, prostate, lung, stomach, pancreas),
- as medicinal product for treating disorders of the neurodegenerative type such as Parkinson's disease, Huntington's chorea, Alzheimer's disease, multiple sclerosis or motor neuron disease,
- as medicinal product for treating diseases connected with cerebral development (holoprosencephaly), for treatment of cerebrovascular accident and for cardiovascular accidents, as well as for diseases of the oligodendrocytes and Schwann cells, for use in vitro for controlling and modulating the renewal of human or animal stem cells, as medicinal product for treating other disorders in which modulation of the Hedgehog signalling pathway could be beneficial, for example diabetes.

The posology to be used will vary depending on the disorder to be treated, the route and frequency of administration, as well as the nature and the weight of the species to be treated (human or animal); it can vary for example from 10 mg to 2 g per day in an adult by the oral route.

The present invention further relates to a pharmaceutical composition, characterized in that it comprises, as active principle, at least one compound of formula (I) as defined above, and at least one pharmaceutically acceptable excipient.

Among the pharmaceutical compositions according to the invention, the compound or compounds of formula (I) are preferably used in an amount allowing unit doses between about 10 mg and 2 g to be administered.

A person skilled in the art will select one or more pharmaceutically acceptable excipients in relation to the route of administration of the pharmaceutical composition. Of course, a person skilled in the art will in that case make sure that the excipient or excipients used are compatible with the intrinsic properties of the composition according to the present invention.

Moreover, the form of the medicinal product or of the pharmaceutical composition (for example, a solution, a suspension, an emulsion, tablets, capsules, suppositories, etc.) will depend on the chosen route of administration.

Thus, in the sense of the present invention, the medicinal product or the pharmaceutical composition can be administered by any suitable route, for example by the oral, anal, local, systemic, intravenous, intramuscular or mucosal route, or else using a patch, or else in a form encapsulated in, or immobilized on, liposomes, microparticles, microcapsules, and the like.

We may notably mention, as nonlimiting examples of suitable excipients for administration by the oral route, talc, lactose, starch and derivatives thereof, cellulose and derivatives thereof, polyethylene glycols, polymers of acrylic acid, gelatin, magnesium stearate, animal, vegetable or synthetic fats, paraffin derivatives, glycols, stabilizers, preservatives, antioxidants, wetting agents, anti-agglomerating agents, dispersants, emulsifiers, taste correctants, penetrating agents, solubilizing agents, etc.

The techniques for formulating and administering medicinal products and pharmaceutical compositions are well known in the technical field considered here, and a person skilled in the art can notably refer to the work Remington's Pharmaceutical Sciences (21$^{st}$ edition).

The compounds of formula (I) of the invention prove to be extremely useful both as tools for the discovery of new modulators of these signalling pathways and for detecting different forms of the Smoothened receptor or of related receptors and identifying molecules capable of modulating these various forms.

The present invention therefore also relates to the use of at least one labeled compound of formula (I) as a research tool, notably for identifying molecules capable of interacting with the Smoothened receptor or a related receptor, for example by binding to the Smo1 binding site or to the Smo2 binding site.

In fact, the inventors found quite unexpectedly that the introduction of a marker on one end of structural fragments of the compounds of formula (I) could lead to radioligands exhibiting a subnanomolar affinity characterized in many bioassays.

The labeling of the compounds of formula (I) can be radioactive by incorporating radioactive isotopes such as $^3$H, $^{11}$C, $^{14}$C, $^{32}$P, $^{35}$S, $^{125}$I, $^{99m}$Tc, $^{18}$F, $^{64}$Cu, $^{76}$Br, $^{124}$I, $^{13}$N, $^{15}$O or $^{123}$I according to the conventional methods of the prior art. The labeling of the compound of formula (I) can also consist of fixation of a fluorophore on said compound by the methods known by a person skilled in the art; the labeling can be detected conventionally using radio-imagers selected as a function of the radioactive atom to be detected, or by measuring the fluorescence.

Several radioligands of the signalling pathway are described in the literature, but are still little used. For example, the radioligands labeled with tritium $^3$H or with iodine $^{125}$I such as $^3$H SAG (Rominger et al., JPET, 2009, 995-1005), $^3$H-Hh-Ag1.5 (Borzillo and Lippa., Curr. Top Med. Chem., 2005, 5(2), 147-57), [$^3$H]GDC-0449 (Dijkgraaf et al., 2011, Cancer Res. 435-444) or the AP-cyclopamine [$^3$H]-cyclopamine (Chen et al., Genes Dev., 2002, 16: 2743-2748):

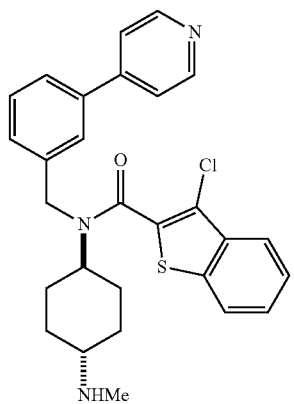

$^3$H SAG

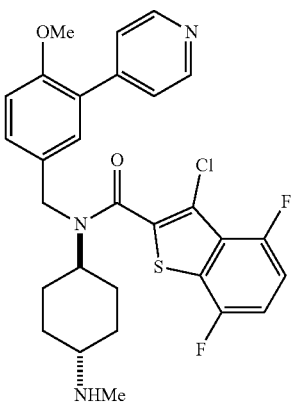

$^3$H Hh-Ag 1.5

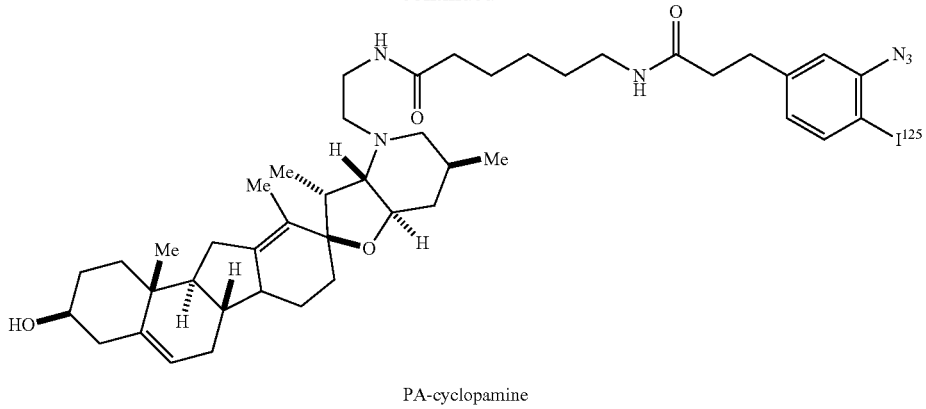

PA-cyclopamine

A series of analogs were studied, with the aim of obtaining a substance labeled with tritium for conducting experiments of specific binding and/or of autoradiography for a deeper analysis of the mechanism of action of the modulators of receptors of the Hedgehog protein signalling pathway, and more particularly of the Smoothened receptor. In fact, the labeled compounds previously described in the prior art are not easily accessible; they require a large number of synthesis steps. Moreover, among the radioligands described above, only the AP-cyclopamine [$^3$H]-cyclopamine is available commercially. Moreover, it exhibits low affinity (Kd of about 10 nM) (Rominger et al., JPET, 2009, 995-1005), in contrast to the compounds of the invention (Kd=0.3 nM for compound (7d)).

More particularly, the compounds of formula (I) in labeled form can be used:

for detecting tumors associated with hyperactivation of the Hedgehog protein signalling pathway, for screening and/or identifying ligands of specific binding sites of the receptors of the Hedgehog protein signalling pathway, such as the Smoothened receptor or related receptors such as the Frizzled receptors (Frizzled 1 to 10), or else as the Patched (Patched 1 and Patched 2), Dispatched (Dispatched 1 and Dispatched 2) or Hip receptors, where said receptors of the Hedgehog protein signalling pathway can be expressed naturally or can be transfected (plasmid gene transfer) or infected (by using viruses) stably or transiently in primary cells, cell lines or healthy or pathological tissues, for screening and/or identifying new molecules that are antagonists of the receptors of the Hedgehog protein signalling pathway (anticancer molecules) or agonists of the receptors of the Hedgehog protein signalling pathway acting on the stem cells, in autoradiography for analyzing the functioning of the Hedgehog protein signalling pathway in primary cells, cell lines or healthy or pathological tissues, for studying pharmacological regulation of the receptors of the Hedgehog protein signalling pathway in primary cells, cell lines or healthy or pathological tissues.

Another object of the present invention relates to a method of radiolabeling a compound of formula (I) as defined above comprising a step of tritiating a compound of formula (I) under an atmosphere of tritium $^3$H, with said method comprising a preliminary step of halogenation when the compound of formula (I) is substituted with a group $R_5$ that does not have an ethylenic double bond.

Thus, an additional object of the present invention relates to a compound of formula (I) obtainable by the method of radiolabeling described above, in which at least one of its hydrogen atoms has been replaced with a tritium atom $^3$H. These compounds of formula (I) radiolabeled with tritium $^3$H can be used as research tools, and for the various uses enumerated above.

Various methods for screening modulators of the Hedgehog pathway are known:

methods using cellular responses of primary lines or cultures: cellular differentiation (C3H10T1/2), cellular proliferation (primary cerebellar granule cells);

methods using competition with a fluorescent compound acting on the transmembrane domains of the targeted receptor [(bodipycyclopamine (BC)] (US 2007/0218775);

methods using a reporter gene of the pathway involved (Taipale et al., 2000, Nature, 406, 1005-1009);

a test detecting Hh activity by measuring the Ptc-Hh interactions in the presence or absence of the test compound (US 2005/0282231);

a test using cells defective for Sufu and a reporter for identifying inhibitors of the Hh pathway acting downstream of Smo (WO 2006/080894).

The present invention also relates to a method of screening and/or identifying ligands of the Smo binding sites (Smo1 or Smo2) of the Smoothened receptor comprising the following steps:

a) bringing in contact the Smoothened receptor and at least one compound of formula (I) to obtain a complex [Smo-compound of formula (I)];

b) bringing in contact the Smoothened receptor, said compound of formula (I) and a test molecule;

c) detecting interaction between said Smoothened receptor and said test molecules by comparing the Smoothened receptor recovered in step b) with the complex [Smo-compound of formula (I)]; and d) selecting said test molecules for which interaction with the Smoothened receptor is measured.

Step a) can be carried out with cells expressing the Smoothened receptor or with extracts of membranes comprising the functional Smoothened receptor; they can notably be extracts of membranes of yeasts bearing the functional Smoothened human receptor obtainable by the method described by Rivoyre et al. (FEBS Letters 579, 2005, 1529-1533).

When step a) is carried out with cells expressing the Smoothened receptor, expression of said receptor is either constitutive (the receptor is expressed naturally by the cell), or it results from the transformation of a cell so that it expresses or overexpresses a Smoothened receptor of the same species or of a different species. This Smoothened receptor can also carry a mutation that endows it with biochemical or pharmacological properties different than the wild-type receptor.

Any compound of formula (I) can be used for carrying out the method according to the invention; however, it can be selected by a person skilled in the art notably in relation to its affinity for the Smoothened receptor.

Step a) can be carried out in the liquid phase or on a suitable solid support; a person skilled in the art will select and will adapt these embodiments for example according to whether the Smoothened receptor is used in the form of extracts of membranes or in the form of purified protein.

When step a) is carried out in the liquid phase, the method of liquid-phase screening can be carried out according to the following steps:

a) bringing in contact the Smoothened receptor and at least one compound of formula (I) to obtain a complex [Smo-compound of formula (I)];

b) bringing in contact the Smoothened receptor, said compound of formula (I) and a test molecule;

c) recovering said Smoothened receptor optionally bound to one or more test molecules and/or to said compound of formula (I);

d) detecting interaction between said Smoothened receptor and said test molecules by comparing the Smoothened receptor recovered in step c) with the complex [Smo-compound of formula (0]; and e) selecting said test molecules for which an interaction is measured.

Step a) can be carried out with membrane extracts comprising the Smoothened receptor, which are then incubated with the compound of formula (I) and the test molecules; the mixture is then centrifuged; the pellet obtained after centrifugation is resuspended in a buffer, then centrifuged again to eliminate the nonspecific interactions. The fixation of the test molecule on the Smoothened receptor is then analyzed either by measurement of fluorescence, or by measurement of radioactivity depending on the labeling of the compound of formula (I):

according to one variant of the method of liquid-phase screening, said compound of formula (I) is labeled beforehand. Step d) of detecting the interaction between the Smoothened receptor and one or more of the test molecules is carried out by comparing the labeling (by radioactivity or fluorescence) of the Smoothened receptors recovered in step c) with that of the complex [Smo-compound of formula (I)]; the molecules selected are those for which the labeling of the Smoothened receptors recovered in step c) is weaker than that of the complex [Smo-compound of formula (I)];

according to another variant of the method of liquid-phase screening, interaction is detected by chromatography by comparing the position of the complex [Smo-compound of formula (I)] with that of the Smoothened receptor recovered in step c); if the position is identical then there is no interaction between the Smoothened receptor and the test molecule. Conversely, a difference of position indicates an interaction, and it is then necessary to confirm that the interaction between the test molecule and the Smoothened receptor does indeed take place on a Smo binding site.

Step a) of the method of screening according to the invention can alternatively be carried out on a suitable solid support.

Solid support means in particular a biosensor consisting of a membrane that comprises a biological species, such as an enzyme, an antibody, a peptide, a microorganism, a biological tissue, a lipid, a nucleic acid etc., allowing binding to a test molecule and a transducer for transforming the biological signal, such as the fixation of a ligand on a protein receptor, into a measurable physical signal, for example electrochemical (amperometric, potentiometric, conductometric), optical (light), piezoelectric or calorimetric. In the present case, the biological species fixed on the membrane is the Smoothened receptor; in two experiments conducted in parallel, the Smoothened receptor on a solid support is brought in contact with a compound of formula (I) and with the mixture of said compound of formula (I) and a test molecule, and the signals obtained in each of these experiments are compared; the molecules that induce a modification of the signal are selected.

As an example, the solid support is a biosensor for detecting binding by plasmon resonance, use of which allows visualization and characterization (affinity, association and dissociation constants) of the interactions between a protein and its ligand by change in mass on the surface of the biosensor. This change of mass is measured by variations of the plasmon resonance angle on the surface of the biosensor and does not require a labeled or fluorescent ligand.

When the method of screening on a solid support is carried out with extracts of membranes comprising the Smoothened receptor, these extracts can be fixed by injection on a lipophilic biosensor. When a lipophilic biosensor is used, the membrane extracts are fixed to the lipophilic groups bound by covalent bonds to dextran, allowing monitoring of the interaction between membrane receptors and ligands (M. R. Pourshafie et al., J. Microbiol. Meth., 2004, 58, 313-320; A. Wikstrom, Anal. Biochem., 2007, 362, 98-107).

Thus, according to one variant of the invention, the biosensor for detecting binding by plasmon resonance is a lipophilic biosensor such as a "sensorchip L1" hydrophobic biosensor from Biacore (GE Healthcare), on which a preparation of membranes containing the Smoothened receptor is fixed by injection.

When the method of screening on a solid support is carried out with the purified Smoothened receptor, said receptor can also be fixed on a biosensor allowing measurement of surface plasmon resonance that consists of detecting a change in the index of the interface on which the receptor is fixed when a ligand is fixed there.

According to another variant, the method of screening on a solid support also makes it possible to identify ligands of the Smoothened receptor that do not bind to a Smo binding site; the activating or inhibiting action of these ligands can be characterized by the methods presented below.

The present invention also relates to a method of identifying agonists of the Smoothened receptor, which, in addition to the steps described for the method of ligand identification, comprises the additional steps of bringing the ligand identified in contact with a cell that displays a cellular response following activation of the Smoothened receptor and selecting the agonist molecules capable of inducing said cellular response of said cell.

The cells that display a cellular response following activation of the Smoothened receptor are selected from the primary lines or cultures: mesenchymal cells (for example, C3H10T1/2) responding to activation of the Smoothened receptor by cellular differentiation measurable by the activity of alkaline phosphatase; primary cerebellar granule cells responding to activation of the Smoothened receptor by cellular proliferation; stem cells of the adult brain or neural progenitors or else progenitor cells present in the tissues during development or in the adult for which the cellular response can, for example, consist of the induction of genes such as those coding for the transcription factors of the Gli family, or else for Patched or Hip, genes activated by the Hedgehog pathway.

The present invention also relates to a method of identifying a molecule that is an antagonist of the Smoothened receptor comprising the following steps:

a) culturing cells that display a cellular response following activation of the Smoothened receptor with at least one compound of formula (I) so as to induce said cellular response;

b) bringing the cells obtained at the end of step a) in contact with a test molecule;

c) selecting the molecules inducing inhibition of said cellular response of said cells.

The molecule whose antagonist activity of the Smoothened receptor we wish to test can notably be a ligand that binds to a Smo binding site of the Smoothened receptor identified by any one of the above methods for ligand identification according to the invention.

The present invention further relates to a kit for carrying out the methods according to the invention comprising at least the functional Smoothened receptor and at least one compound of formula (I). The functional Smoothened receptor is either present in the form of membrane extract, or in cells that display a cellular response following activation of the Smoothened receptor.

Binding experiments between the Smoothened receptor and a compound of formula (I) can also be used for characterizing and identifying:

new cellular types expressing the Smoothened receptor in a conformation where the Smo binding site is active;

receptors involved in differentiation, such as receptors related to the Smoothened receptor.

The invention thus relates to a method of identifying cells, such as tumor cells, expressing the Smoothened receptor comprising the steps of:

a) bringing cells to be tested in contact with a labeled compound of formula (I);

b) cleaning the cells in order to remove said labeled compound of formula (I) that has not bound to any receptor of the cells to be tested;

c) detecting the labeled cells.

The compounds can also serve for identifying and for characterizing new receptors or new forms of receptors involved in cellular differentiation, proliferation, cell death, migration, cellular survival or else allowing the cell to acquire a property or a state that it has not yet attained.

BRIEF DESCRIPTION OF THE DRAWINGS

Besides the foregoing provisions, the invention further comprises other provisions that will become clear from the description given below, which refers to examples of synthesis, of characterization and of evaluation of compounds of formula (I) according to the invention, and to the labeling thereof, as well as to the appended drawings in which:

FIGS. 1A and 1B show the activity of the compounds on differentiation of the C3H10T1/2 cells (FIG. 1A), and on proliferation of the PCGs of rat cerebellum (FIG. 1B). The inhibition curves were generated with increasing concentrations of the molecules studied in the presence of SAG (0.1 µM, FIG. 1A and 0.01 µM, FIG. 1B). The values are expressed as percentage of the maximum response induced by SAG. FIG. 1C illustrates inhibition of binding of bodipy-cyclopamine (BC) by the different compounds. The HEK-hSmo cells are incubated with BC (5 nM) alone (control) or in the presence of an increasing concentration of the molecules under investigation. The binding of BC is visualized by fluorescence microscopy and the dose-response curve of the compounds is obtained after quantification. The values are expressed as percentage of specific binding of BC. The data correspond to the values (mean values±SEM) obtained from an experiment representative of 2-4 independent experiments, FIG. 3A: The membranes of HEK-hSmo cells (2 µg of proteins) were incubated in a final volume of 0.4 ml of HEPES 0.2% BSA buffer with increasing concentrations of compound $^3$H-(7d) for 3 hours at 37° C. The nonspecific binding was evaluated in the presence of 1 µM of GDC-0449. Analysis of the specific binding gives values of $K_d$ of 0.3±0.1 nM and of $B_{max}$ of 1086±91 cpm. The data are the mean values±SEM of triplicates (representative experiment, n=3). FIG. 3B: Scatchard analysis of the specific binding of the compound $^3$H-(7d)

DETAILED DESCRIPTION

Example 1

Figure 1:
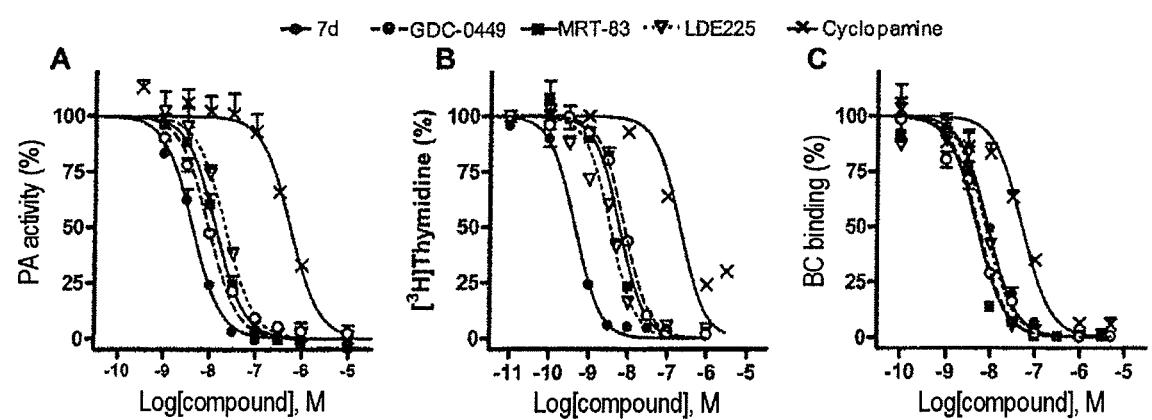
FIG. 1 illustrates the activity of compound (7d) and of the reference compounds in various cellular tests and on the binding of bodipy-cyclopamine (BC) to the Smo receptor.

Protocols for Synthesis and Characterization of Various Compounds According to the Invention The reactions were carried out under atmosphere of inert gas (nitrogen) using Schlenk techniques (standard). The solvents were dried by standard methods and were distilled under nitrogen before use. All the reagents were obtained commercially and used as such without preliminary purification.

The mass spectrometries (ESI+) were recorded on an LC/MSD spectrometer sold under the reference Agilent® 1100. The nuclear magnetic resonance (NMR) spectra were

A/ Preparation of a Compound of Formula IV

Preparation of 3,4,5-trimethoxy-N—(N-(4-methyl-3-nitrophenyl)carbamimidoyl)benzamide (3)

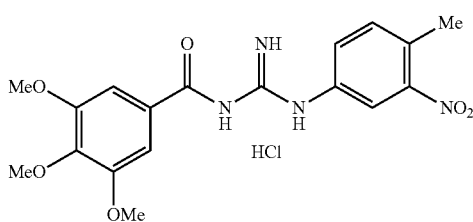

A solution of cyanamide (2) (1.12 g, 4.77 mmol) and of 4-methyl-3-nitro aniline (A1) in the form of hydrochloride [1.08 g, 5.72 mmol, prepared by adding 1 eq. of HCl (2M in Et₂O) to aniline in MeOH (10 mL), followed by concentration under vacuum to obtain a powder] in toluene (50 mL) is heated under reflux for 6 hours with stirring. A solid forms. Et₂O (50 mL) is added to promote precipitation. The solid is filtered and dried under vacuum; then the solid is dissolved in a saturated aqueous solution of NaHCO₃ in H₂O (30 mL). The aqueous solution is extracted with Et₂O (2×50 mL). The organic phase is washed with brine, dried over Na₂SO₄ and concentrated to obtain nitro-guanidine (3) (1.22 g, 66%).

$^1$H-NMR (CDCl$_3$, 300 MHz) δ=7.80 (brs, 1H), 7.34-7.27 (m, 5H), 3.90 (s, 9H).

MW=388 for $C_{18}H_{20}N_4O_6$ [ES/MS] m/z 389 [M+1]$^+$

B/ Preparation of a Compound of Formula V

Preparation of tert-butyl(4-methyl-3-nitrophenylamino) (3,4,5-trimethoxybenzamido)methylenecarbamate (4)

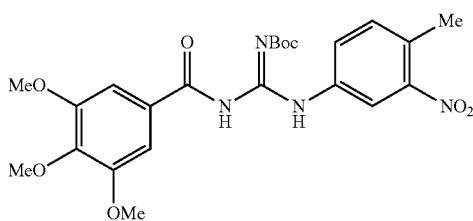

A solution of Boc₂O (1.77 g, 8.13 mmol) in THF (10 mL) at room temperature and DMAP (97 mg, 1 mmol) as catalyst is added dropwise to a solution of guanidine in the form of base (3) (3.16 g, 8.13 mmol) in THF (90 mL). After stirring for 1 hour, the starting compound had been consumed. The solvent is evacuated under vacuum, and the residue is purified by column chromatography, eluting with EtOAc/Hept mixture: 3/7. Boc-guanidine is obtained in the form of oil (4) (2.3 g, 58%).

$^1$H-NMR (CDCl$_3$, 300 MHz) δ=7.27 (s, 1H), 7.09-7.04 (m, 3H), 6.59 (m, 2H), 3.82 (s, 3H), 3.70 (s, 6H), 2.17 (s, 4H), 1.39 (s, 9H).

MW=488 for $C_{23}H_{28}N_4O_8$ [ES/MS] m/z 489 [M+1]$^+$

C/ Preparation of a Compound of Formula VI

Preparation of tert-butyl(3-amino-4-methylphenylamino) (3,4,5-trimethoxybenzamido)methylenecarbamate (5)

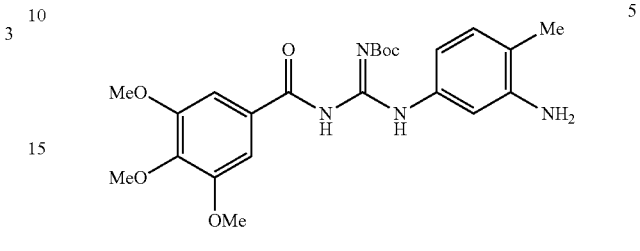

In a bottle, a mixture of Boc nitro-guanidine (4) (1.22 g, 2.5 mmol) in MeOH (80 mL) and Pd/C 10% (100 mg) is stirred under H₂ at 50 psi for 10 hours. The starting substrate has disappeared; the catalyst is filtered and the solvent is evacuated under vacuum. The residue is purified by column chromatography, eluting with Hept/EtOAc mixture: 7/3, obtaining the title compound as yellow oil (5) (840 mg, 73%).

$^1$H-NMR (CDCl$_3$, 300 MHz) δ=7.27 (s, 1H), 7.09-7.04 (m, 3H), 6.59 (m, 2H), 3.82 (s, 3H), 3.70 (s, 6H), 2.17 (s, 3H), 1.39 (s, 9H).

MW=458 for $C_{23}H_{30}N_4O_6$ [ES/MS] m/z 459 [M+1]$^+$

D/ Preparation of Various Compounds of Formulas (6) and (7)

D-1) Preparation of tert-butyl(3-(4-benzoylbenzamido)-4-methylphenylamino) (3,4,5-trimethoxybenzamido)methylenecarbamate (6a)

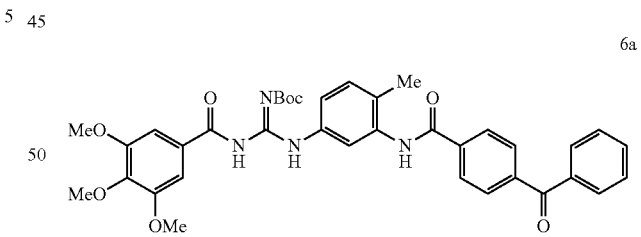

A solution of acid chloride (1a) (73 mg, 0.3 mmol) in CH₂Cl₂ (3 mL) at 0° C. is added dropwise to a solution of Boc guanidine (5) (137 mg, 0.3 mmol) and triethylamine (0.1 mL, 0.66 mmol) in CH₂Cl₂ (10 mL). The reaction mixture is stirred overnight. Water (15 mL) and CH₂Cl₂ (10 mL) are added. The organic phase is washed with brine, dried and concentrated under vacuum. The residue is purified by silica gel column chromatography, eluting with Hept/EtOAc mixture: 3/2. The title compound is obtained in the form of a white solid (6a) (142 mg, 70%, Mp 96° C.).

¹H-NMR (CDCl₃, 300 MHz) δ=10.47 (brs, 1H), 9.33 (brs, 1H), 8.01-7.82 (m, 8H), 7.55-7.53 (m, 3H), 7.29-7.10 (m, 3H), 3.82 (s, 3H), 3.71 (s, 6H), 2.41 (s, 3H), 1.44 (s, 9H).

D-2) Preparation of N—(N-(3-(4-benzoylbenzamido)-4-methylphenyl)carbamimidoyl)-3,4,5-trimethoxybenzamide hydrochloride (7a)

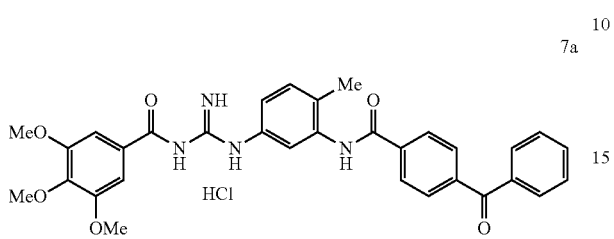

7a

A solution of Boc-guanidine (6a) (85 mg, 0.127 mmol) in a mixture of AcOH (1 mL) and concentrated HCl (0.5 mL) is stirred overnight. The reaction mixture is concentrated under vacuum, taken up in Et₂O, and concentrated again, giving a white solid (7a) (72 m, 94%, Mp 138° C.).

¹H-NMR (MeOH, d4, 400 MHz) δ=8.16 (d, J=8 Hz, 2H), 7.93 (d, J=8 Hz, 2H), 7.85-7.34 (m, 9H), 3.97 (m, 6H), 3.89 (s, 3H), 2.43 (s, 3H).

MW=566 for C₃₂H₃₀N₄O₆ [ES/MS] m/z 567 [M+1]⁺

D-3) Preparation of tert-butyl(3-(9H-fluorene-2-carboxamido)-4-methylphenylamino) (3,4,5-trimethoxybenzamido)methylenecarbamate (6b)

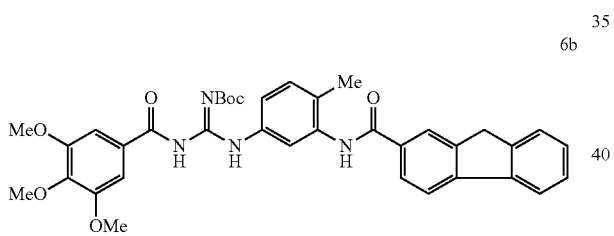

6b

The acid chloride (1b) (82 mg, 0.3 mmol) in solution in CH₂Cl₂ (3 mL) is added dropwise to a solution of Boc-guanidine (5) (137 mg, 0.3 mmol) and triethylamine (0.05 mL, 0.36 mmol) in CH₂Cl₂ (10 mL). The mixture is stirred overnight, then water (5 mL) and CH₂Cl₂ (10 mL) are added. The organic phase is treated with brine, dried and concentrated under vacuum. The oily residue is purified by column chromatography, eluting with Hept/Et₂O mixture: 3/2, obtaining the title compound (6b) (109 mg, 56%).

¹H-NMR (CDCl₃, 300 MHz) δ=10.47 (bs, 1H), 9.37 (m, 1H), 8.07-7.02 (m, 13H), 3.99 (s, 2H), 3.81 (s, 3H), 3.71 (s, 6H), 2.41 (s, 3H), 1.43 (s, 9H)

D-4) Preparation of N-(2-methyl-5-(3-(3,4,5-trimethoxybenzoyl)guanidino)phenyl)-9H-fluorene-2-carboxamide hydrochloride (7b)

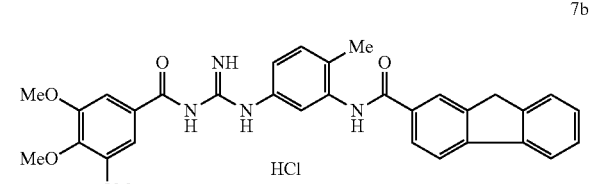

7b

The compound Boc (6b) (100 mg, 0.154 mmol) is dissolved in a mixture of AcOH (1.1 mL) and concentrated HCl (0.55 mL). The mixture is stirred for 4 hours at room temperature. The solvent is evaporated under vacuum and the solid residue is taken up in Et₂O, then filtered, recovering a white solid (7b) (72 mg, 80%, Mp 241° C.)

¹H-NMR (DMSO, d6, 400 MHz) δ=12.24 (brs, 1H), 11.53 (brs, 1H), 10.2 (s, 1H), 9.42 (brs, 1H), 8.95 (brs, 1H), 8.23-7.40 (m, 12H), 4.05 (s, 2H), 3.91 (s, 6H), 3.78 (s, 3H), 2.35 (s, 3H).

MW=550 for C₃₂H₃₀N₄O₅ [ES/MS] m/z 551 [M+1]⁺

D-5) Preparation of tert-butyl(4-methyl-3-(4-(3-phenylpropyl)benzamido)phenylamino) (3,4,5-trimethoxybenzamido)methylenecarbamate (6c)

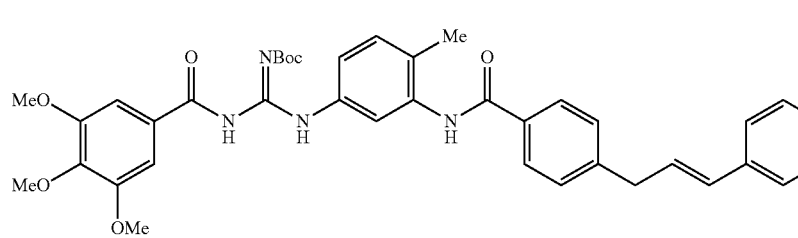

6c

A solution of the acid chloride (1c) (73 mg, 0.3 mmol) in CH$_2$Cl$_2$ (3 mL) is added at room temperature to a solution of Boc-guanidine (5) (137 mg, 0.3 mmol) and triethylamine (0.1 mL, 0.66 mmol) in CH$_2$Cl$_2$ (10 ml). Leave the reaction mixture overnight. Add water (8 mL) and CH$_2$Cl$_2$ (10 mL). Wash the organic phase with saturated NaCl solution. Then the organic phase is dried and concentrated under vacuum. The residue is purified on a silica gel column, eluting with EtOAc/Hept mixture: 2/3. The title compound is obtained in the form of a white solid (6c) (132 mg, 65%).

$^1$H-NMR (CDCl$_3$, 300 MHz) δ=10.47 (brs, 1H), 9.37 (brs, 1H), 8.02-7.01 (m, 18H), 3.81 (s, 3H), 3.69 (s, 6H) 2.72-2.64 (m, 4H), 2.05-1.92 (m, 2H), 1.42 (s, 9H)

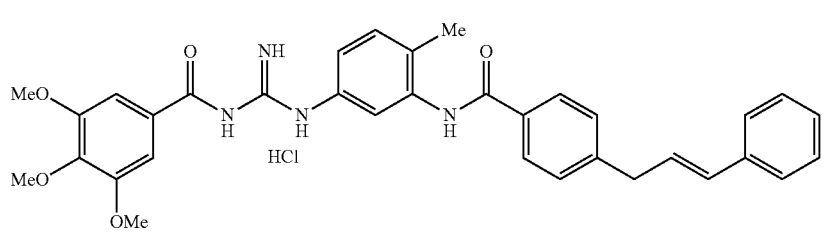

7c

D-6) Preparation of 3,4,5-trimethoxy-N—(N-(4-methyl-3-(4-(3-phenylpropyl)benzamido)phenyl)carbamimidoyl)benzamide hydrochloride (7c)

A solution of the compound Boc (6c) (116 mg, 0.17 mmol) in a mixture of AcOH (1.5 mL) and concentrated HCl (0.75 mL) is stirred at room temperature for 4 hours. The solvent is then evaporated and the residue is taken up in Et$_2$O. The title compound is recovered as a white solid (80 mg, 82%, Mp 132° C.).

MW=580 for C$_{34}$H$_{36}$N$_4$O$_5$ [ES/MS] m/z 581 [M+1]$^+$

D-7) Preparation of tert-butyl(4-methyl-3-(4-phenethylbenzamido)phenylamino) (3,4,5-trimethoxybenzamido)methylenecarbamate (6d)

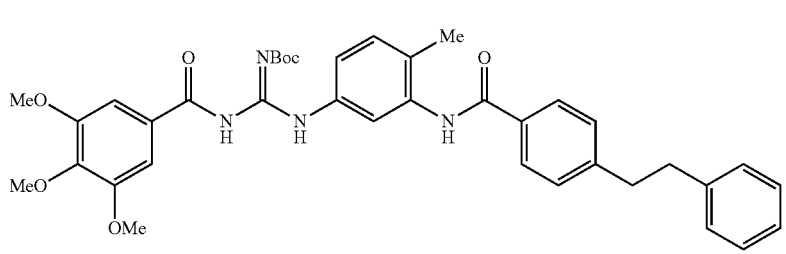

6d

A solution of acid chloride (1d) (80 mg, 0.33 mmol) is added at room temperature to a solution of Boc-guanidine used as base (5) (137 mg, 0.3 mmol) and triethylamine (0.06 mL, 0.45 mmol) in CH$_2$Cl$_2$ (10 mL). The solution is stirred overnight, and CH$_2$Cl$_2$ is added (10 mL), as well as H$_2$O (10 mL). The organic phase is washed with brine, dried and concentrated under vacuum. The residue is purified by silica gel column chromatography, eluting with EtOAc/Hept:2/3, obtaining the title compound (6d) in the form of a solid (150 mg, 75%, Mp 161° C.).

$^1$H-NMR (CDCl$_3$, 300 MHz) δ=10.47 (brs, 1H), 9.37 (brs, 1H), 8.02-7.68 (m, 4H), 7.29-7.01 (m, 11H), 3.81 (s, 3H), 3.68 (s, 6H), 3.01-2.96 (m, 4H), 2.37 (s, 3H) 1.42 (s, 9H).

MW=666 for C$_{38}$H$_{42}$N$_4$O$_7$ [ES/MS] m/z 667 [M+1]$^+$

D-8) Preparation of 3,4,5-trimethoxy-N—(N-(4-methyl-3-(4-phenethylbenzamido)phenyl)carbamimidoyl)benzamide hydrochloride (7d)

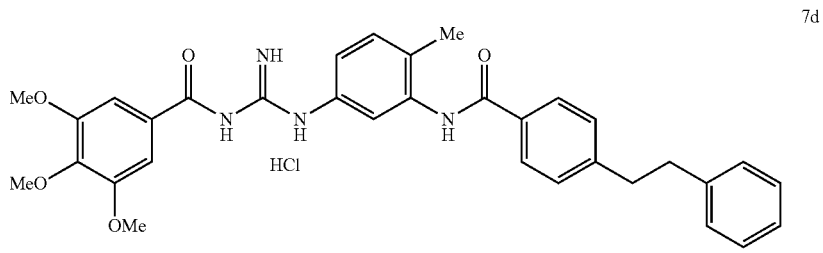 [SMILES: COc1cc(C(=O)NC(=N)Nc2ccc(C)c(NC(=O)c3ccc(CCc4ccccc4)cc3)c2)cc(OC)c1OC ; Cl]

7d

A solution of the adduct Boc (6d) (120 mg, 0.18 mmol) in a mixture of AcOH (1.3 mL) and concentrated HCl (0.66 mL) is stirred at room temperature for 4 hours. The solvent is evaporated under vacuum, and the residue is taken up in Et$_2$O (10 mL) and filtered, obtaining a white powder (7d) (101 mg, 93%, Mp 186° C.).

$^1$H-NMR (MeOH, d4, 300 MHz) δ=7.90 (d, 2H J=8 Hz), 7.52-7.16 (m, 12H), 3.95 (s, 6H), 3.87 (s, 3H), 3.03-2.99 (m, 4H), 2.38 (s, 3H).

MW=566 for C$_{33}$H$_{34}$N$_4$O$_5$ [ES/MS] m/z 567 [M+1]$^+$

D-9) Preparation of tert-butyl(3-(4-cinnamylbenzamido)-4-methylphenylamino) (3,4,5-trimethoxybenzamido)methylenecarbamate (6e)

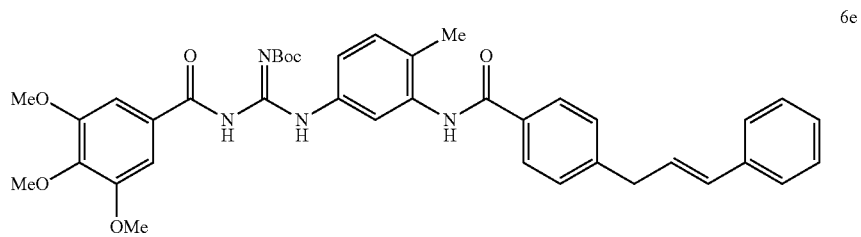

6e

A solution of the acid chloride (1e) (73 mg, 0.3 mmol) in CH$_2$Cl$_2$ (3 mL) is added at room temperature to a solution of Boc-guanidine (5) (137 mg, 0.3 mmol) and triethylamine (0.1 mL, 0.66 mmol) in CH$_2$Cl$_2$ (10 ml). Leave the reaction mixture overnight. Add water (8 mL) and CH$_2$Cl$_2$ (10 mL). Wash the organic phase with saturated NaCl solution. Then the organic phase is dried and concentrated under vacuum. The residue is purified on a silica gel column, eluting with EtOAc/Hept mixture: 1/4. The title compound is obtained in the form of a white solid (6e) (142 mg, 70%).

$^1$H-NMR (CDCl$_3$, 300 MHz) δ=10.47 (brs, 1H), 9.36 (brs, 1H), 8.02-7.01 (m, 17H), 6.51-6.32 (m, 2H), 3.81 (s, 3H), 3.69 (s, 6H), 3.62 (m, 2H), 2.36 (s, 3H), 1.42 (s, 9H)

D-10) Preparation of (E)-N—(N-(3-(4-cinnamylbenzamido)-4-methylphenyl)carbamimidoyl)-3,4,5-trimethoxybenzamide hydrochloride (7e)

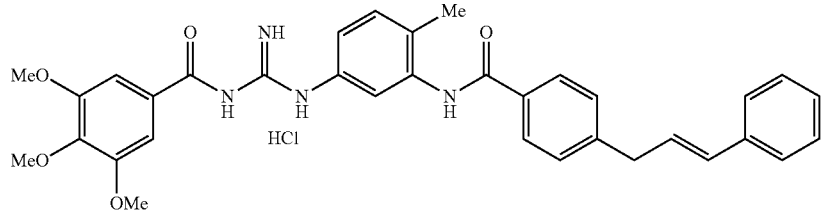

7e

A solution of the compound Boc (6e) (122 mg, 0.15 mmol) in a mixture of AcOH (1.5 mL) and concentrated HCl (0.75 mL) is stirred at room temperature for 4 hours. The solvent is then evaporated and the residue is taken up in Et$_2$O. The title compound is recovered in the form of white solid (7e) (101 mg, 91%, Mp 127° C.).

$^1$H-NMR (MeOD, d4, 400 MHz) δ=7.98-7.94 (m, 2H), 7.52-7.28 (m, 12H), 6.49-6.43 (m, 2H), 3.95 (s, 6H), 3.65 (s, 3H), 3.66-3.64 (m, 2H), 2.38 (s, 3H).

MW=578 for C$_{34}$H$_{34}$N$_4$O$_5$ [ES/MS] m/z 579 [M+1]$^+$

D-11) Preparation of tert-butyl(4-methyl-3-(4-styrylbenzamido)phenylamino) (3,4,5-trimethoxybenzamido)methylenecarbamate (6f)

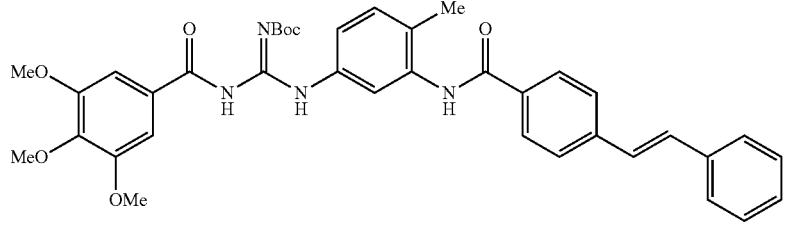

6f

A solution of the acid chloride (1f) in CH$_2$Cl$_2$ (3 mL) is added to a solution of Boc guanidine (5) (137 mg, 0.3 mmol) and triethylamine (0.1 mL, 0.66 mmol) in CH$_2$Cl$_2$ (10 mL), then the reaction mixture is left to react overnight. Water (10 mL) and CH$_2$Cl$_2$ (15 mL) are then added. The organic phase is decanted and washed with a solution of NaCl (saturated, in H$_2$O), dried, evaporated and purified by silica gel column chromatography, eluting with EtOAc/Hept mixture: 3/7, obtaining the title compound in the form of a white solid (6f) (130 mg, 65%, Mp 166° C.).

$^1$H-NMR (CDCl$_3$, 300 MHz) δ=10.47 (brs, 1H), 9.35 (brs, 1H), 8.02-7.09 (m, 17H), 3.81 (s, 3H), 3.71 (s, 6H), 2.39 (s, 3H), 1.43 (s, 9H).

D-12) Preparation of N—(N-(3-(4-benzylbenzamido)-4-methylphenyl)carbamimidoyl)-3,4,5-trimethoxybenzamide hydrochloride (7f)

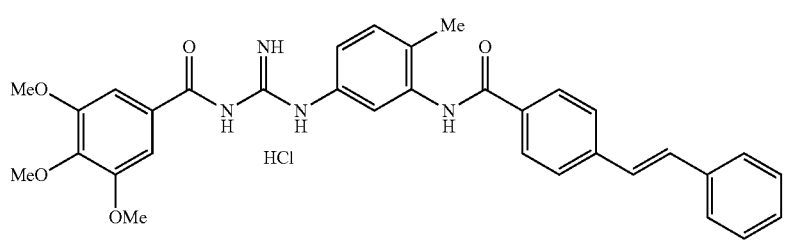

7f

A solution of the compound Boc (6f) (120 mg, 0.18 mmol) in a mixture of AcOH (3 mL) and concentrated HCl (1.5 mL) is stirred at room temperature for 2 hours. The solvent is then evaporated and the residue is taken up in Et$_2$O, obtaining a white solid (70 mg, 70%, Mp 221° C.).

$^1$H-NMR (MeOD, d4, 300 MHz) δ=8.02-7.29 (m, 16H), 3.94 (s, 6H), 3.87 (s, 3H), 2.40 (s, 3H).

MW=564 for C$_{35}$H$_{32}$N$_4$O$_5$ [ES/MS] m/z 565 [M+1]$^+$

D-13) Preparation of tert-butyl(3-(4-benzylbenzamido)-4-methylphenylamino) (3,4,5-trimethoxybenzamido)methylenecarbamate (6 g)

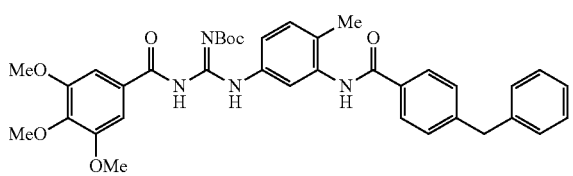

6g

A solution of the acid chloride (1 g) (73 mg, 0.3 mmol) in CH$_2$Cl$_2$ (3 mL) at room temperature is added to a solution of Boc-guanidine (5) (137 mg, 0.3 mmol) and triethylamine (0.1 mL, 0.66 mmol) in CH$_2$Cl$_2$ (10 ml). The mixture is left to react overnight. Water (8 mL) and CH$_2$Cl$_2$ (10 mL) are then added. The organic phase is washed with saturated NaCl solution, then dried and concentrated under vacuum. The residue is purified on a silica gel column, eluting with EtOAc/Hept mixture: 1/8. The title compound is obtained in the form of a white solid (6 g) (144 mg, 71%, Mp 105° C.).

$^1$H-NMR (CDCl$_3$, 300 MHz) δ=10.47 (brs, 1H), 9.35 (brs, 1H), 8.01-7.07 (m, 16H), 4.06 (s, 2H), 3.80 (s, 3H), 3.68 (s, 6H), 2.31 (s, 3H).

D-14) Preparation of N—(N-(3-(4-benzylbenzamido)-4-methylphenyl)carbamimidoyl)-3,4,5-trimethoxybenzamide hydrochloride (7 g)

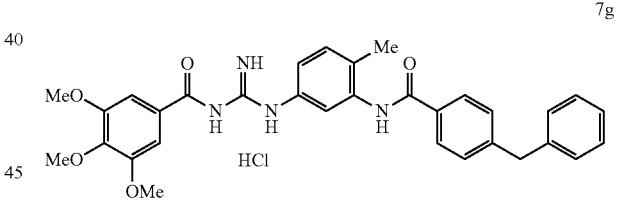

7g

A solution of the compound Boc (7e) (103 mg, 0.15 mmol) in a mixture of AcOH (1.5 mL) and concentrated HCl (0.75 mL) is stirred at room temperature for 4 hours. The solvent is then evaporated and the residue is taken up in Et$_2$O. The title compound is recovered in the form of white solid (7 g) (85 mg, 90%, Mp 112° C.).

$^1$H-NMR (MeOD, d4, 400 MHz) δ=7.95 (d, J=8 Hz, 1H), 7.53-7.23 (m, 12H), 4.09 (s, 2H), 3.36 (s, 6H), 3.86 (s, 3H), 2.39 (s, 3H).

MW=552 for C$_{32}$H$_{32}$N$_4$O$_5$ [ES/MS] m/z 553 [M+1]$^+$

D-15) Preparation of tert-butyl(3-(4-(benzyloxy)benzamido)-4-methylphenylamino) (3,4,5-trimethoxybenzamido)methylenecarbamate (6h)

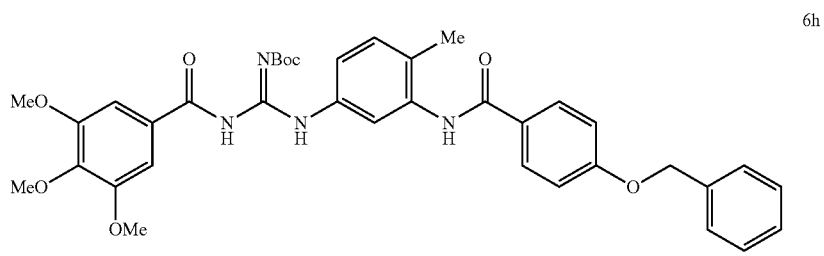

6h

A solution of the acid chloride (1h) (73 mg, 0.3 mmol) in CH$_2$Cl$_2$ (3 mL) at room temperature is added to a solution of Boc-guanidine (5) (137 mg, 0.3 mmol) and triethylamine (0.1 mL, 0.66 mmol) in CH$_2$Cl$_2$ (10 ml). The mixture is left to react overnight. Water (8 mL) and CH$_2$Cl$_2$ (10 mL) are then added. The organic phase is washed with saturated NaCl solution, then dried and concentrated under vacuum. The residue is purified on a silica gel column, eluting with EtOAc/Hept mixture: 1/4. The title compound is obtained in the form of a white solid (6h) (103 mg, 68%, Mp 94° C.).

D-16) Preparation of N—(N-(3-(4-(benzyloxy)benzamido)-4-methylphenyl)carbamimidoyl)-3,4,5-trimethoxybenzamide hydrochloride (7h)

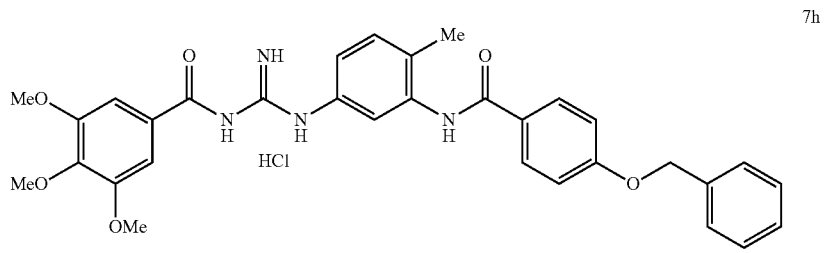 [SMILES: COc1cc(C(=O)NC(=N)Nc2ccc(C)c(NC(=O)c3ccc(OCc4ccccc4)cc3)c2)cc(OC)c1OC ; Cl]

7h

A solution of the compound Boc (6h) (116 mg, 0.18 mmol) in a mixture of AcOH (1.5 mL) and concentrated HCl (0.75 mL) is stirred at room temperature for 4 hours. The solvent is then evaporated and the residue is taken up in Et$_2$O. The title compound is recovered in the form of white solid (7h) (80 mg, 82%, Mp 192° C.).

$^1$H-NMR (MeOH, d6, 300 MHz) δ=8.02-7.99 (m, 2H), 7.54-7.16 (m, 11H), 5.23 (s, 2H), 3.97 (s, 6H), 3.88 (s, 3H), 2.39 (s, 3H)

MW=568 for C$_{32}$H$_{32}$N$_4$O$_6$ [ES/MS] m/z 569 [M+1]$^+$

E/Radiolabeling of Compounds of Formula (I)

E-1) Hydrogenation of Compound (7f) to Compound (7d)

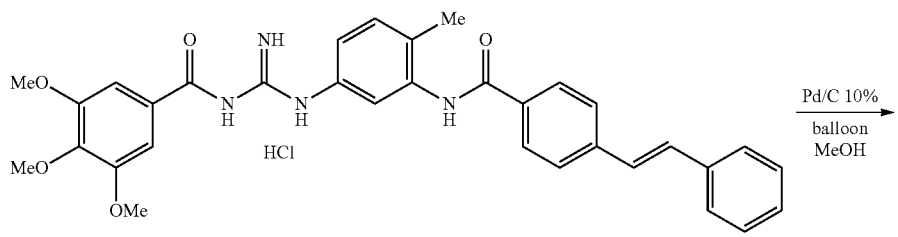

7f

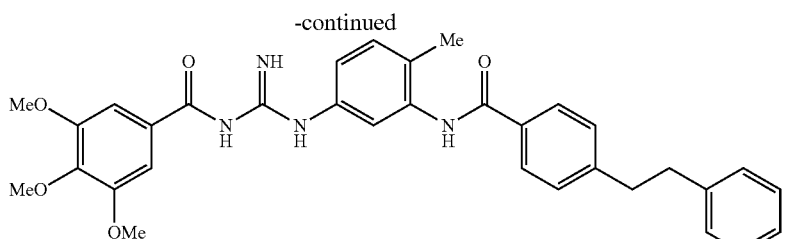

7d

A solution of the compound (70 in the form of hydrochloride salt (5 mg, 0.08 mmol) in MeOH and Pd/C (10%) is stirred under hydrogen (balloon) for 4 hours. The mixture is then filtered and concentrated under vacuum to obtain compound (7d) in the form of hydrochloride salt.

MW=566 for $C_{33}H_{34}N_4O_5$ [ES/MS] m/z 567 [M+1]$^+$ and 565 [M−1]$^+$

E-2) Tritiation of the Compound (70 to $^3$H-(7d)

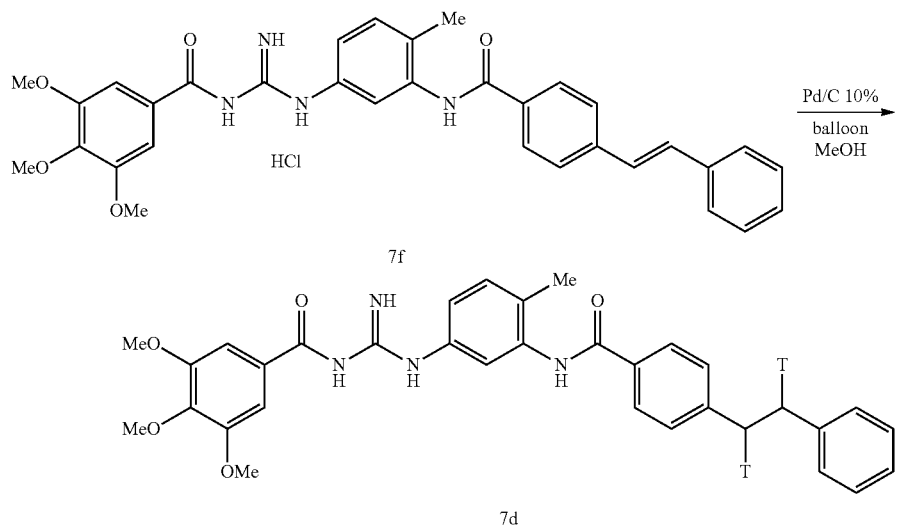

In a 5-mL balloon flask, the compound (70 (2.5 mg, 0.04 mmol) is dissolved in MeOH (1 mL) and the solution is cooled (liquid nitrogen). The catalyst (Pd/C 10%) is dispersed on the surface. Once a vacuum is created in the flask, tritium gas is introduced until a pressure of 30 psi is reached. The reaction mixture is stirred for 3 hours. The catalyst is filtered and the excess tritium is evacuated under vacuum with MeOH. The product (7d) is obtained directly without purification.

Characteristics of the Compound [$^3$H]-(7d):
Purity: >98% (HPLC)
Specific activity: 38.1 Ci/mmol (1.41 TBq/mmol)
Concentration: 1.0 mCi/ml (37 MBq/ml)
Chromatographic Data:
HPLC column: Macherey+Nagel Nucleodur Gravit)' C8, (5 flm), 4.6×150 mm
Mobile phase: A: water 0.05% TFA; B: MeCN 0.05% TFA
Gradient: 0 min 30% B; 10 min 95% B; 14 min 95% B; 14 min 95% B; 14.5 min 30%
Flow: 1.0 ml/min Sample: 1.30 mCi/ml in methanol (48.1 MBq/ml)
Injection: 5.0 µl (6.5 µCi, 240 KBq)
UV detection: 254 nm
Temperature: 30° C.
Radio-detector: Berthold LB 513
Cocktail: Zinsser Quicksz int Flow 302
Flow: 2.0 mL/min
Retention time: 7.17 min (UV); 7.30 min (radio-detector) (the difference between the two retention times is due to installation of the 2 detectors in series).

Example 2

Demonstration of the Modulating Effect of the Compounds of Formula (I) on the Hedgehog Protein Signalling Pathway and of Fixation Thereof on the Smoothened Receptor The effect of the compounds of formula (I) according to the invention on inhibition of the Hedgehog protein signalling pathway was determined in vitro by analyzing the differentiation of the line of pluripotent fibroblast C3H10T1/2 cells after activation of this pathway in these cells by a synthetic activator: SAG. The activity of the compound X was also evaluated from the growth of a primary culture of cerebellar granule cells. The capacity of this last-mentioned compound for binding to the mouse Smoothened receptor was also determined by competition with body-cyclopamine, a fluorescent compound derived from cyclopamine that binds to the transmembrane domains of the receptor, as described by Chen et al., Genes Dev., 2002, 16, 2743.

1—Material and Methods

Inhibition of the Hedgehog Pathway by the Compounds of Formula (I) on the C3H10T1/2 Cells:

The test compounds of formula (I) were dissolved in dimethylsulfoxide up to a concentration of 10 mM, then stored at a temperature of −20° C. until used.

The line of C3H10T1/2 pluripotent fibroblast cells (ATCC) was cultured in the conditions recommended by the ATCC. These cells were activated using 0.1 µM of SAG according to the methods described by Chen et al., Proc. Natl. Acad. Sci. USA, 2002, 99, 14071 and Frank-Kamenetsky et al., J. Biol., 2002, 1, 10.

Activation by SAG causes differentiation of the cell line and allows it to express alkaline phosphatase (AP). It was thus possible to measure the activity of the Hedgehog protein signalling pathway via measurement of the alkaline phosphatase (AP) activity.

The C3H10T1/2 cells were seeded on 96-well plates at a density of $5.10^3$ cells per well, 24 hours before adding the test compounds at a concentration varying from 1 nM to 30 µM and in the presence of 0.1 µM of SAG, using DMEM (Dulbecco's Modified Eagle's Medium) with 10% fetal calf serum as culture medium. The tests were carried out in quadruplicate. The plates were then incubated for 5 to 6 days at a temperature of 37° C. under 5% $CO_2$ atmosphere. The cells were then washed in cold phosphate buffer ("Phosphate Buffer Serum": PBS), then lysed by sonication at 4° C. in 50 µL of a solution containing 0.9% of NaCl and 0.2% of Triton X-100.

For comparison, the activity of other known inhibitors of the Hedgehog protein signalling pathway were tested in the same conditions as were used for testing the various compounds of formula (I) according to the invention:

cyclopamine, as described by Incardona et al., Development, 1998, 125, 3553, corresponding to the following formula:

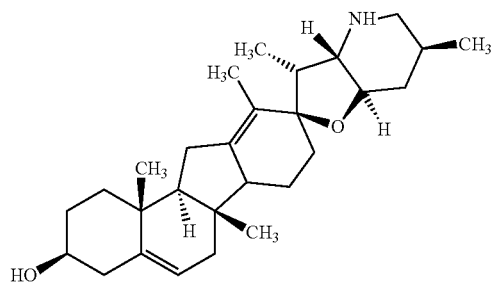

MRT-83 described above, and

LDE225, such as described by Pan and Dorsch; ACS Med. Chem. Lett., 2010, 1: 130-134, corresponding to the following formula:

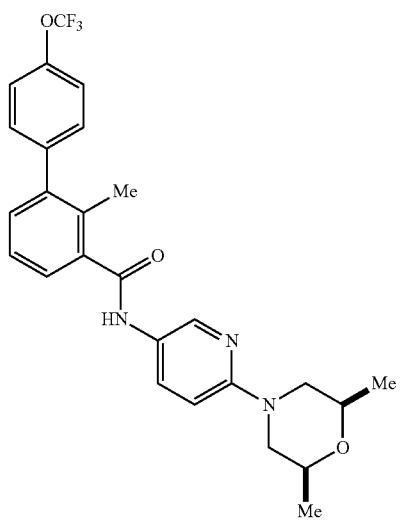 [SMILES: Cc1c(C(=O)Nc2ccc(N3C[C@@H](C)O[C@@H](C)C3)nc2)cccc1-c1ccc(OC(F)(F)F)cc1]

Measurement of the alkaline phosphatase (AP) activity in the lysates thus obtained was then performed according to the method described by Pepinsky et al. (J. Biol. Chem., 1998, 273, 14037). After adding 100 µL of reaction buffer (200 mM Tris-HCl; pH 10.5; 0.4 M of 2-amino-2-methylpropanol and 8 mM of $MgCl_2$) and 50 µL of substrate (4 mM of p-nitrophenyl disodium phosphate), the lysates were incubated at 37° C. for 30-60 min, then the optical density was read at a wavelength of 415 nm.

Activity of the Compounds of Formula (I) on Proliferation of the Precursors of the Cerebellar Granule Cells:

The granule cell precursors (GCP) are isolated from cerebellums of rats (IFFA-CREDO, France), 8 days after birth (P8). The cerebellums are taken, cut into small pieces, placed in Krebs-Ringer buffer (120 mM NaCl, 5 mM KCl, 1 mM $KH_2PO_4$, 25 mM $NaHCO_3$, 15 mM glucose, 0.04 mM phenol red) and incubated for 15 minutes at room temperature in a dissociation buffer composed of Krebs-Ringer with addition of 250 mg/ml of trypsin (Sigma, France). Enzymatic dissociation is stopped by adding an equal volume of Krebs-Ringer buffer containing 250 mg/ml of a trypsin inhibitor and 80 mg/ml of DNase (Sigma, France). The tissue is centrifuged at 100 g for 10 seconds and the pellet obtained is resuspended and triturated using Pasteur pipettes of decreasing diameter to obtain a suspension of isolated cells. This suspension is centrifuged at 200 g for 5 minutes and the pellet obtained is resuspended in Neurobasal medium supplemented with 1 mM of pyruvate, 2 mM L-glutamine, penicillin/streptomycin and 1% of supplement N2, 60 mg/ml N-acetyl cysteine and 100 mg/ml of bovine serum albumin (BSA, Sigma, France).

The cerebellar GCPs obtained are transferred to 96-well plates treated beforehand with poly-D-lysine at a density of $2.10^5$ cells/well. SAG in the presence or absence of the other test compounds is added immediately. 12 hours before the end of culture, tritiated thymidine ($^3$H-thymidine) is added. The cells are aspirated and recovered on a glass fiber filter (GF/C) using an automated cell collector (Brandel, USA). The amount of radioactivity incorporated by the cells was quantified in the presence of a scintillating agent in a liquid scintillation counter (Wallac, USA).

Competition of the Compounds of Formula (I) with Bodipy-Cyclopamine (BC):

Cells of the HEK293 line stably transfected with the human Smo receptor are used. The experiment was conducted according to the protocol described in Roudaut et al., Mol. Pharmacol. 79: 453-460, 2011. The inhibition of the binding of bodipy-cyclopamine (BC) by the compounds of formula (I) is measured by the decrease in fluorescence photographed and quantified using the Simple PCI 6.2 software (Hamamatsu Corporation), then referred to the surface area of the nuclei present on the photograph.

Test of Radio-Binding of the Tritiated Compound $^3$H-(7d):

The binding test is carried out on membranes enriched with Smoothened receptor. Cells of the HEK-hSmo line were used for preparing these membranes. The cells are washed and recovered in iced PBS. After centrifugation at 100 g for 7 minutes at 4° C., the pellet is taken up in 10 times its volume of an iced buffer A (50 mM HEPES, pH 7.4, 1 mM EDTA) with addition of 10 µl of a cocktail of protease inhibitors (PEAK, Sigma) per ml of buffer, then it is homogenized using a Polytron grinding mill. After centrifugation at 500 g for 30 minutes at 4° C., which makes it possible to remove the nuclei from the cells, the supernatant is centrifuged again at 48 000 g for 45 min at 4° C. The pellet is taken up in 2 ml of buffer A with PEAK added, then the suspension is homogenized using a glass conical grinding mill and is passed through a 23 G needle. Finally, aliquots are placed in Eppendorf tubes and stored at −80° C. The concentration of total protein in the preparation is determined by Lowry's method using BSA for preparing the standard range. This concentration is 10.9 mg/ml.

The membranes are resuspended in a buffer (50 mM HEPES and 3 mM MgCl$_2$) containing 0.2% of BSA. The tests of binding of $^3$H-(7d) are carried out in polypropylene tubes. The membranes (2 µg of proteins) are incubated with the $^3$H-(7d) in the presence or absence of the cold test compounds for 3 hours at 37° C. in a final volume of 400 µl. Incubation is stopped by immersing the tubes in iced water followed by rapid filtration (Brandel) through a glass fiber filtration membrane (GF/C) treated beforehand with 0.3% of polyethylenimine, which can reduce the nonspecific binding of the $^3$H-(7d) to the filtration membrane. The radioactivity retained on the filter is measured in the presence of 3 ml of scintillating agent in a liquid scintillation counter. The specific binding is defined as the binding that can be inhibited by 1 µM of GDC-0449 as described by Romer et al., Cancer Cell, 2004, 6, 229 and corresponding to the following formula:

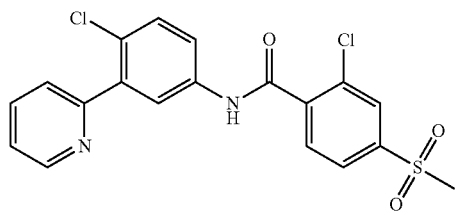 [SMILES: CS(=O)(=O)c1ccc(C(=O)Nc2ccc(Cl)c(-c3ccccn3)c2)c(Cl)c1]

2—Results for the Biological Activity of the Compounds of Formula (I)

Inhibition of the Hedgehog Pathway by the Compounds of Formula (I) on the C3H10T1/2 Cells:

Results obtained with compounds of formula (I) and the reference compounds cyclopamine, LDE225 and MRT-83 are presented in Table 1 below. For each of the compounds, the concentration that can inhibit 50% of the alkaline phosphatase (AP) activity (IC$_{50}$) after induction by SAG at 0.1 µM was evaluated. The inhibition curves obtained with compound (7d) and the reference compounds are shown in FIG. 1A.

TABLE 1

Activity of the compounds on the differentiation of C3H10T1/2 cells

| Compounds | IC$_{50}$ (nM) |
|---|---|
| Cyclopamine* | 620 ± 30 |
| GDC-0449* | 10 ± 1 |
| LDE225* | 22 ± 3 |
| MRT-83* | 11 ± 3 |
| 7a | 32 ± 11 |
| 7b | 28 ± 3 |
| 7c | 39 ± 9 |
| 7d | 6 ± 1 |
| 7e | 57 ± 2 |
| 7f | 15 ± 4 |
| 7g | 220 ± 25 |
| 7h | 72 ± 15 |

*Reference compounds not forming part of the invention

The activity of compound (7d) was also compared with the compound MRT-10 and with various thiourea compounds (compounds 20 to 27 below). The results are summarized in Table 2.

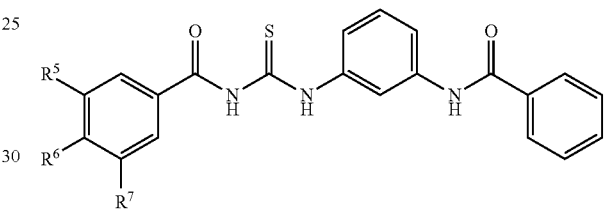

20: $R^5=R^7=$Ome, $R^6=$H; 24: 2-Ome, $R^5=R^7=$H, $R^6=$Ome.
21: $R^5=R^7=$OMe, $R^6=$Oet; 25: $R^5=R^6=R^7=$Oet;
22: $R^5=R^6=$Oet, $R^7=$Ome; 26 $R^5$-$R^6=$—OCH$_2$CH$_2$O—, $R^7=$H;
23: $R^7=$Ome, $R^5$, $R^6=$—OCH$_2$O—; 27: $R^5=R^6=$OMe, $R^7=$H

TABLE 2

Comparison of the activity of the compounds (7d), MRT-10 and of thiourea compounds on the differentiation of C3H10T1/2 cells. C3H10T1/2, (SAG 0.1 µM)

| Compound | IC$_{50}$, µM |
|---|---|
| 7d | 0.006 ± 0.001 |
| MRT-10 | 0.9 ± 0.2 |
| 20 | 1.9 ± 0.2 |
| 21 | 0.6 ± 0.1 |
| 22 | 0.8 ± 0.2 |
| 23 | 1.1 ± 0.6 |
| 24 | 4.1 ± 0.3 |
| 25 | 0.8 ± 0.1 |
| 26 | inactive |
| 27 | >5 |

Mean ± SEM: n ≥ 3

Determination of the Affinity of the Molecules Selected for Proliferation of the Granule Cell Precursors of Rat Cerebellum Induced by SAG:

The cerebellar PCGs proliferate in response to activation of the Shh signalling pathway, a response that can be inhibited by the Smo antagonists (Rohatgi et al., 2009, Proc. Natl. Acad. Sci. USA 106: 3196-201). We therefore analyzed the capacity of compound (7d) for inhibiting the proliferation of the PCGs of rat cerebellum in primary culture by measuring the incorporation of tritiated thymidine, a marker of DNA newly synthesized during the proliferation process. Increasing concentrations of SAG cause a dose-dependent increase in incorporation of the tritiated thymidine above baseline. Compound (7d) displays properties of a complete antagonist with an $IC_{50}$ of 0.45 nM on the proliferation of PCGs induced by SAG (0.01 μM) (FIG. 1B). LDE225, the compound MRT-83 and cyclopamine also block this proliferation but with a weaker affinity, their $IC_{50}$ is 3, 6 and 103 nM respectively (Table 3).

Determination of the Affinity of the Molecules Selected for Binding of Bodipy-Cyclopamine (BC) for the Smoothened Receptor:

To study the properties of binding of compound (7d) to Smo, we analyzed whether this molecule could compete with the binding of bodipy-cyclopamine (BC) (b), which interacts with Smo at the level of these transmembrane domains. The cells are incubated for 2 hours with BC (5 nM) in the presence or absence of different concentrations of compound (7d), MRT-83, LDE225 and cyclopamine. At the end of the incubation, the cells are fixed and stained with DAPI, a fluorescent molecule with high affinity for DNA which makes it possible to visualize the nuclei in blue in fluorescence microscopy. The four molecules tested block the binding of BC to the HEK-hSmo cells, which stably expresses the human Smo receptor, in a dose-dependent manner. It is observed that the affinity of compound (7d) and of MRT-83 remain very similar and high (FIG. 1C). All these data demonstrate that compound (7d) is a powerful antagonist of the human and mouse Smo receptors (Table 1).

TABLE 3

Comparison of the activities of the compounds
(7d), MRT-83, LDE225, GDC-0449 and cyclopamine

| | $IC_{50} \pm SEM$ (nM) | | |
|---|---|---|---|
| | C3H10T1/2 cells (2) | PCGs of rat cerebellum (3) | BC binding (4) |
| Compound (7d) | 6 ± 1 | 0.4 ± 0.1 | 8 ± 1 |
| MRT-83 | 11 ± 3 | 6 ± 1 | 5 ± 3 |
| LDE225 | 22 ± 3 | 3 ± 1 | 8 ± 2 |
| GDC-0449 | 10 ± 3 | 8 ± 1 | 5 ± 2 |
| Cyclopamine | 620 ± 30 | 103 ± 18 | 53 ± 11 |

The $IC_{50}$ values were determined by measuring the activity of the Gli-luciferase reporter induced by ShhN (4 nM) in the Shh-Light2 cells (1), the activity of alkaline phosphatase (AP) associated with differentiation of the C3H10T1/2 cells induced by SAG (0.1 μM) (2), the proliferative activity of the PCGs of rat cerebellum induced by SAG (0.01 μM) followed by the incorporation of $^3$H-thymidine (3), and binding of bodipy-cyclopamine (BC) to the human Smo receptor expressed in the HEK-hSmo cells (4) (according to the curves in FIG. 1).

All of the experiments carried out highlight the capacity of the compounds of formula (I) for modulating the Shh pathway in vitro. Their activity might be explained by binding to the Smoothened protein on a competing site of bodipy-cyclopamine (BC).

3—Results for the Binding Characteristics of the Radioligand $^3$H-(7d)

Figure 2:
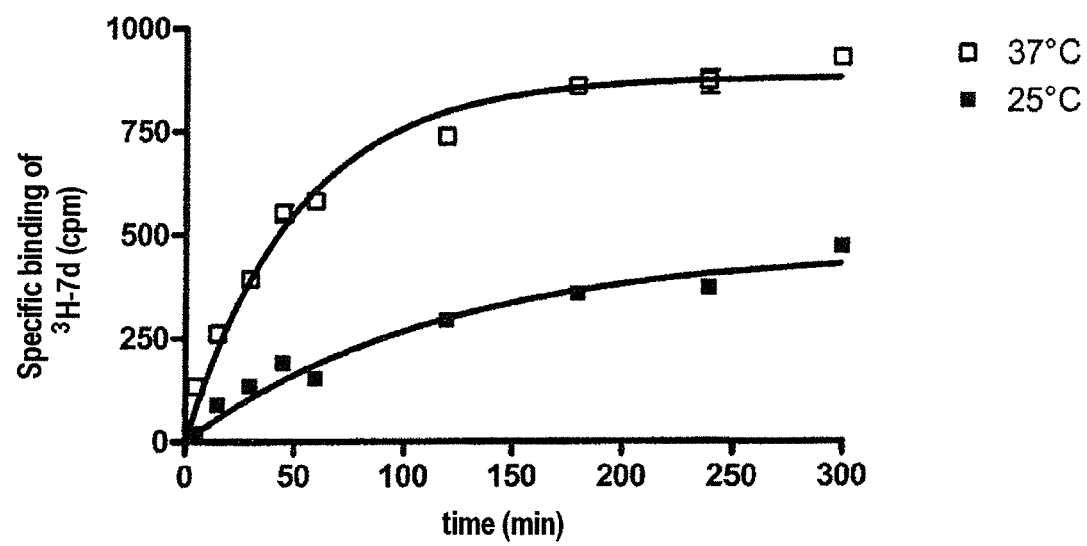
FIG. 2 shows the kinetics of association of the compound $^3$H-(7d) with membranes of HEK-hSmo cells expressing the human Smoothened receptor.

Kinetics of Association of the Radioligand $^3$H-(7d) with the Human Smoothened Receptor:

Compound (7d) is a very powerful antagonist of the Hh signalling pathway, which encouraged us to synthesize the tritiated form of this molecule: the compound $^3$H-(7d). We began the characterization of the properties of this radioligand by studying the kinetics of association of the binding of compound $^3$H-(7d) with homogenates of membranes of HEK293 cells stably expressing the human Smo receptor (HEK-hSmo). Association of the compound $^3$H-(7d) was examined in the presence of a fixed concentration of the radioactive ligand (0.35 nM) and a fixed amount of receptor (2 μg of proteins) at 25° C. and 37° C. for 5 hours. In this experiment, it is a question of determining the time taken for the specific binding of the compound $^3$H-(7d) to reach a state of equilibrium. At 25° C., after 5 hours of incubation, equilibrium has not been reached. At 37° C., equilibrium is reached after 3 hours of incubation and is maintained after 5 hours of incubation (FIG. 2). Beyond 5 minutes of incubation, the nonspecific binding of the compound $^3$H-(7d) (defined in the presence of 0.1 μM of GDC0449) is low (0.4% of the total binding) and remains stable throughout the experiment.

The membranes of HEK-hSmo cells (2 μg of proteins) were incubated in a final volume of 0.4 ml of HEPES buffer (0.2% BSA) with 0.35 nM of $^3$H-(7d) for 5 h at 25° C. (blue) or 37° C. (pink). The nonspecific binding was evaluated in the presence of 1 μM of GDC-0449, a reference Smo antagonist. Analysis of the specific binding by GraphPad Prism gives a half-association time of 33 min at 37° C. and of 71 min at 25° C. The data are the mean values±SEM of triplicates (representative experiment, n=2).

Figure 3:
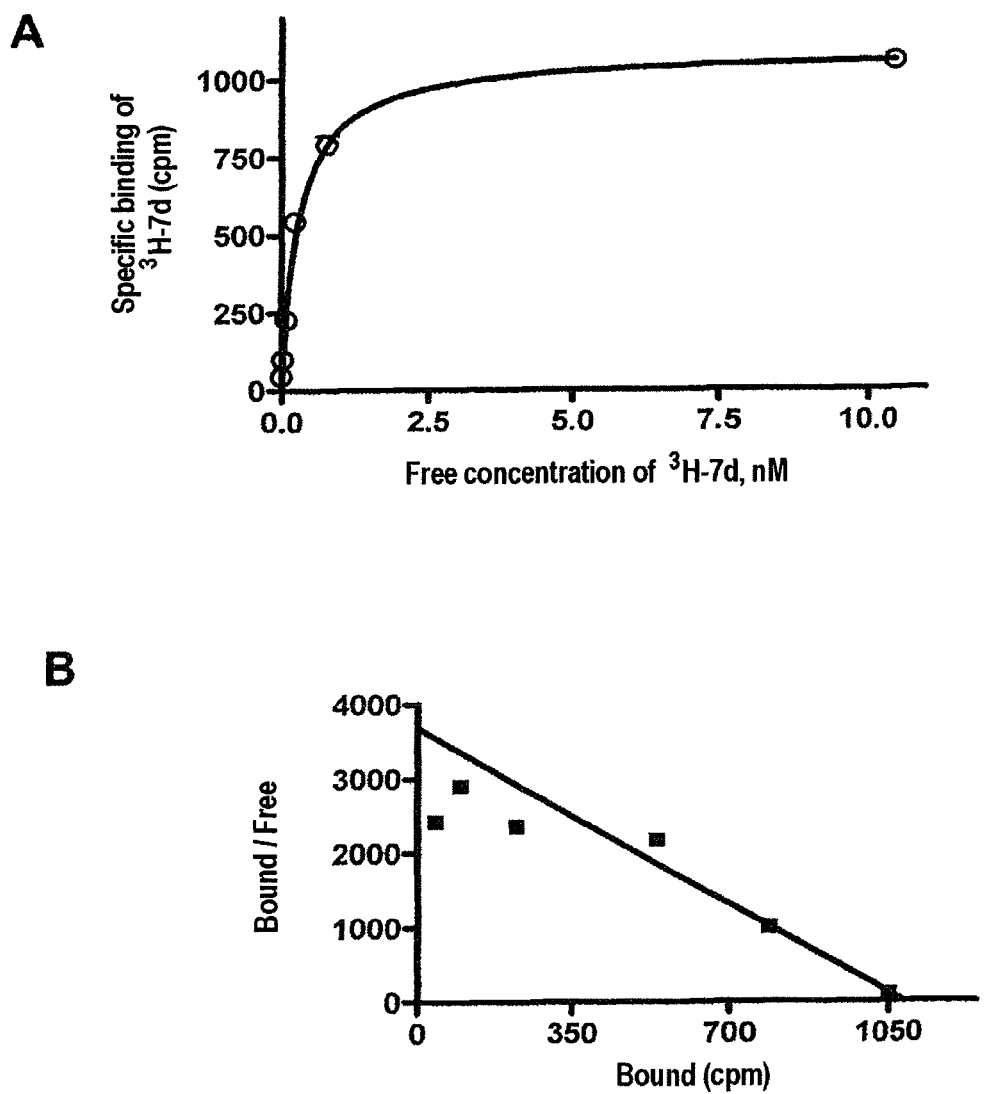
FIG. 3 shows the saturation curve of binding of the compound $^3$H-(7d) to the Smo receptor expressed in the HEK-hSmo cells at equilibrium.

Experiment of Saturation of the Binding of Compound $^3$H-(7d) to the Human Smoothened Receptor:

The properties of compound $^3$H-(7d) were then characterized by studying the saturation of its binding to the Smo receptor expressed in the membranes of the cells of the HEK-hSmo line. It is a question of measuring the specific binding at equilibrium, during incubation of increasing concentrations of the radioactive ligand, with a fixed amount of receptor (2 μg of proteins). The saturation of the specific binding of the compound $^3$H-(7d) to the Smo receptor expressed in the membranes of the HEK-hSmo cells, defined using 1 μM of GDC-0449, is illustrated in FIG. 3A. Analysis of the curve shows a single binding site of high affinity: $K_d$=0.3±0.1 nM and $B_{max}$=1086±91 cpm visualized by the Scatchard representation (FIG. 3B).

In order to be sure that the binding of compound $^3$H-(7d) was indeed specific to the Smo receptor, we also carried out this saturation experiment with membranes of HEK293 cells not transfected with cDNA coding for the human Smo receptor. GDC-0449 (1 μM) has no effect on the binding of compound $^3$H-(7d) to these membranes. Therefore the binding of compound $^3$H-(7d) to the membranes of the HEK-hSmo cells is indeed specific to the Smo receptor.

Figure 4:
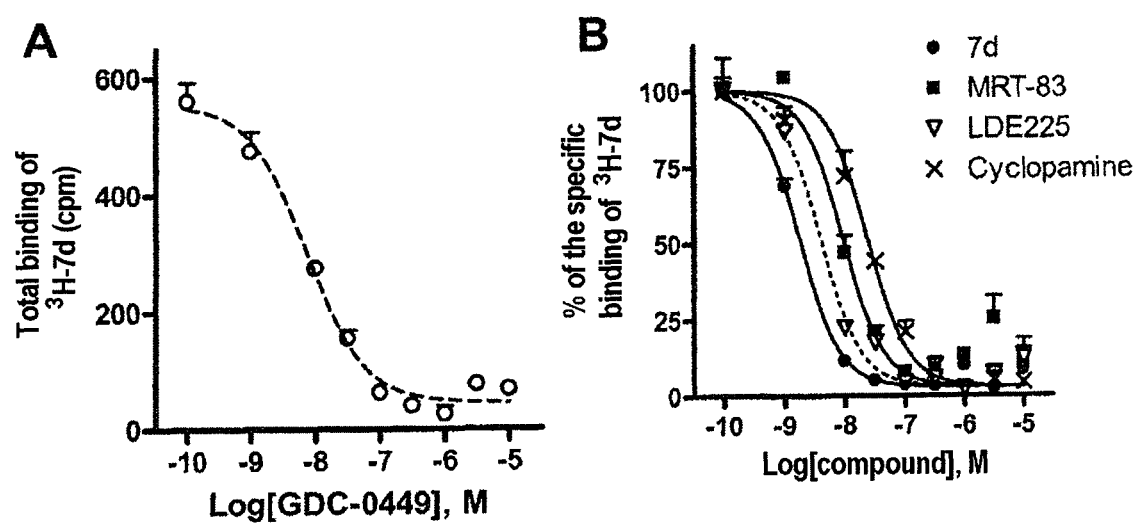
FIG. 4 illustrates inhibition of the binding of the compound $^3$H-(7d) to the human Smoothened receptor expressed in the HEK-hSmo cells. The membranes of HEK-hSmo cells (2 µg of proteins) were incubated for 3 hours at 37° C. in a final volume of 0.4 ml of HEPES buffer (0.2% BSA) with 0.35 nM of compound $^3$H-(7d) alone or in the presence of increasing concentrations of GDC-0449 (A), of compounds (7d), MRT-83, LDE225 and of cyclopamine (B). The data are the mean values±SEM of triplicates (representative experiment, n=2-3) and represent the total binding of the compound $^3$H-(7d) (A) or the percentage specific binding of the compound $^3$H-(7d) determined in the presence of 1 µM of GDC-0449 (B)
Figure 5:
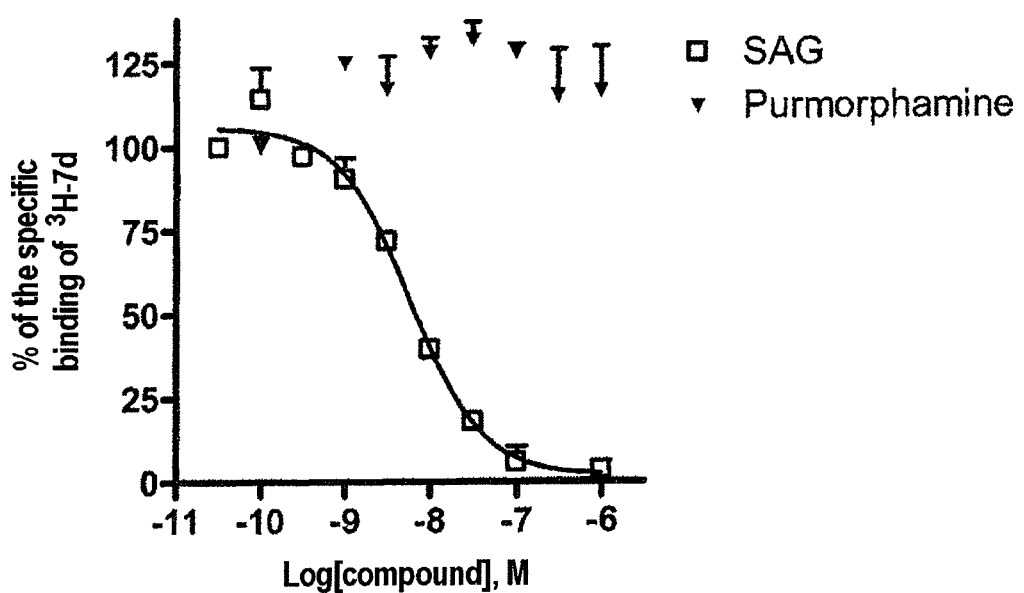
FIG. 5 illustrates inhibition of the binding of the compound $^3$H-(7d) to the human Smoothened receptor expressed in the HEK-hSmo cells by SAG and purmorphamine. The membranes of HEK-hSmo cells (2 µg of proteins) were incubated in a final volume of 0.4 ml of HEPES buffer (0.2% BSA) with 0.35 nM of compound $^3$H-(7d) alone or in the presence of increasing concentrations of SAG or of purmorphamine for 3 hours at 37° C. The data are the mean values±SEM of triplicates (representative experiment, n=2-3) and represent the percentage specific binding of the compound $^3$H-(7d) determined in the presence of 1 µM of GDC-0449.

Pharmacological Analysis of the Binding of Compound $^3$H-(7d) to the Human Smoothened Receptor:

The pharmacology of the binding of compound $^3$H-(7d) to the Smo receptor expressed in the membranes of the cells of the HEK-hSmo line was analyzed in the presence of antagonists and agonists of Smo. In this experiment, the cold ligand competes with the radioactive ligand for binding to the receptor, and the affinity ($K_i$) of each cold ligand for the receptor can be analyzed based on the $IC_{50}$ values deduced from the inhibition curves. The cold compound (7d) is the most powerful for inhibiting the binding of compound $^3$H-(7d) to Smo ($IC_{50}$=1.5 nM). The compounds LDE225, GDC-0449 and MRT-83 have values of $IC_{50}$ of 4 nM, 12 nM and 11 nM, respectively. A concentration of 1 μM of GDC-0449 completely inhibits the specific binding of compound $^3$H-(7d). The nonspecific binding was defined for each experiment in the presence of 1 μM of GDC-0449. Cyclopamine and the compound Cur61414 are also capable of inhibiting the binding of compound $^3$H-(7d) but with a much lower affinity, notably for Cur61414 with a value of IC$_{50}$ of micromolar order (FIG. 4). For the agonists, SAG displays an affinity of nanomolar order (IC$_{50}$=5 nM) whereas purmorphamine is not active (IC$_{50}$>1000) (FIG. 5). The values of K, calculated for the compounds are presented in Table 3.

TABLE 4

Affinities of reference molecules with respect to the binding of compound $^3$H-(7d) to the human Smoothened receptor

| | Binding of compound $^3$H-(7d) | |
|---|---|---|
| | IC$_{50}$ ± SEM (nM) | K$_i$ ± SEM (nM) |
| Compound (7d) | 1.5 ± 0.2 | 0.7 ± 0.1 |
| MRT-83 | 10.5 ± 2.5 | 4.8 ± 1.2 |
| LDE225 | 4.2 ± 0.8 | 1.9 ± 0.3 |
| Cyclopamine | 30 ± 4 | 14 ± 2 |
| GDC-0449 | 12 ± 5 | 6 ± 2 |
| SAG | 5.2 ± 0.8 | 2.4 ± 0.3 |
| Purmorphamine | inactive | inactive |

The values of IC$_{50}$ and K$_i$ were determined by measuring the binding of compound $^3$H-(7d) to the human Smo receptor expressed in the cells of the HEK-hSmo line. The data are the mean values±SEM of 2-3 representative experiments.

The invention claimed is:

1. A compound, characterized in that it corresponds to the following formula (I):

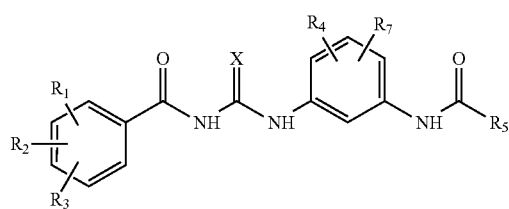

(I)

in which:
  R$_1$, R$_2$ and R$_3$, which may be identical or different, independently of one another, represent a hydrogen or halogen atom, a hydroxyl radical, an alkyl, perfluoroalkyl, alkoxy, alkylthio or nitrile group,
  X represents O, S or NH,
  R$_4$ and R$_7$, which may be identical or different, independently of one another, represent a hydrogen or halogen atom or an alkyl group,
  R$_5$ represents one of the groups selected from:

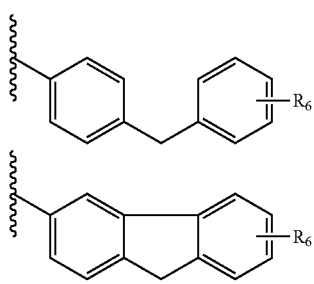

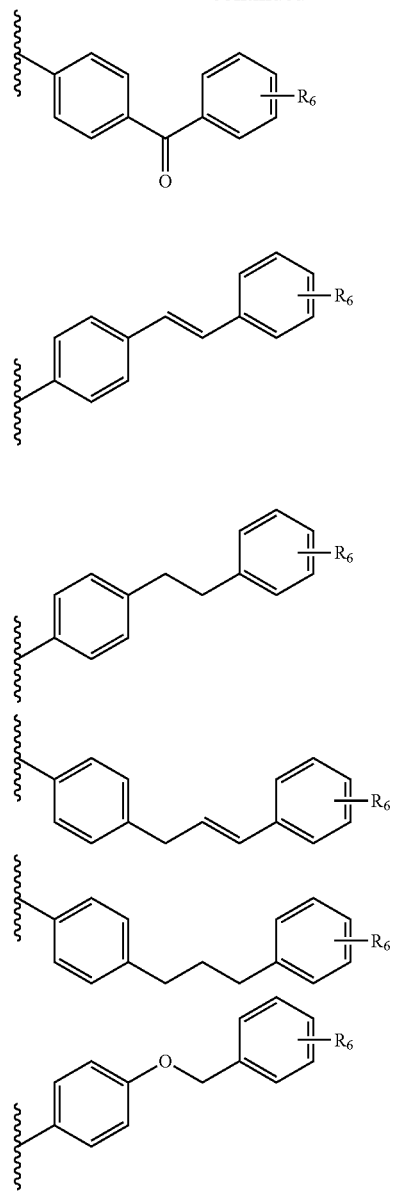

substituted with at least one radical R$_6$ representing a halogen atom or an alkyl, alkoxy, aminoalkyl, thioalkyl or hydroxyl group.

2. The compound of formula (I) as claimed in claim 1, characterized in that R$_1$, R$_2$ and R$_3$ represent an alkoxy radical, and preferably a methoxy radical.

3. The compound of formula (I) as claimed in claim 1, characterized in that X is NH.

4. The compound of formula (I) as claimed in claim 1, characterized in that R$_4$ and R$_7$ represent a hydrogen or chlorine atom, a methyl, ethyl or isopropyl group.

5. The compound of formula (I) as claimed in claim 1, characterized in that R$_6$ represents a halogen atom or an alkoxy or aminoalkyl group.

6. The compound of formula (I) as claimed in claim 1, characterized in that the compound is selected from the group consisting of:

N—(N-(3-(4-benzoylbenzamido)-4-methylphenyl)carbamimidoyl)-3,4,5-trimethoxybenzamide hydrochloride of the following formula:

(Compound 7a)

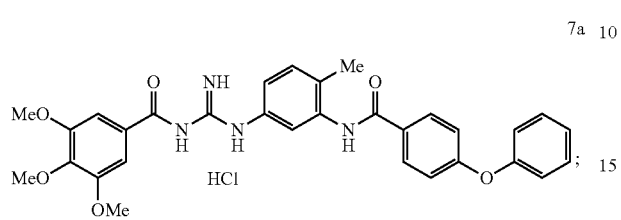

N—(N-(3-(4-benzoylbenzamido)-4-methylphenyl)carbamimidoyl)-3,4,5-trimethoxybenzamide hydrochloride of the following formula:

(Compound 7b)

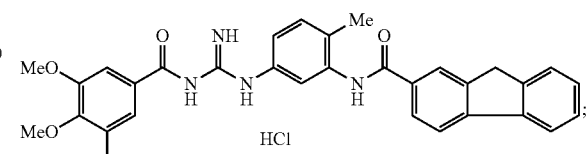

3,4,5-trimethoxy-N—(N-(4-methyl-3-(4-(3-phenylpropyl)benzamido)phenyl)carbamimidoyl)benzamide of the following formula:

(Compound 7c)

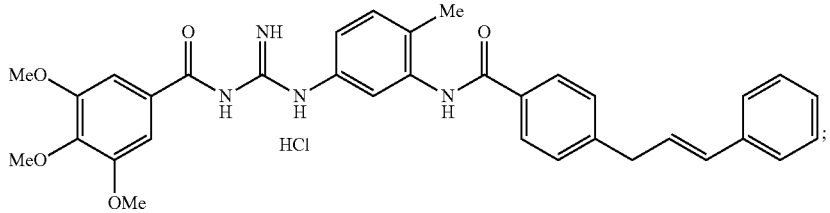

3,4,5-trimethoxy-N—(N-(4-methyl-3-(4-phenethylbenzamido)phenyl)carbamimidoyl)benzamide of the following formula:

(Compound 7d)

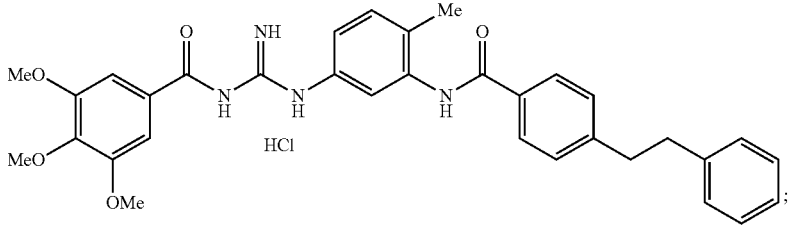

(E)-N—(N-(3-(4-cinnamylbenzamido)-4-methylphenyl)carbamimidoyl)-3,4,5-trimethoxybenzamide hydrochloride of the following formula:

(Compound 7e)

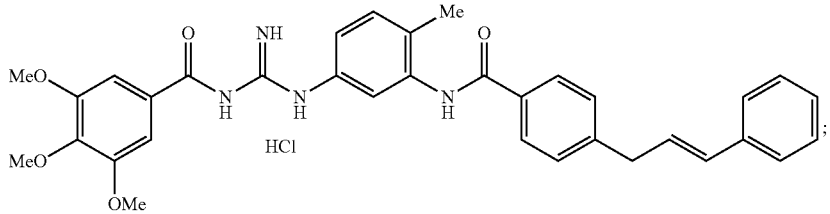

N—(N-(3-(4-benzylbenzamido)-4-methylphenyl)carbamimidoyl)-3,4,5-trimethoxybenzamide hydrochloride of the following formula:

(Compound 7f)

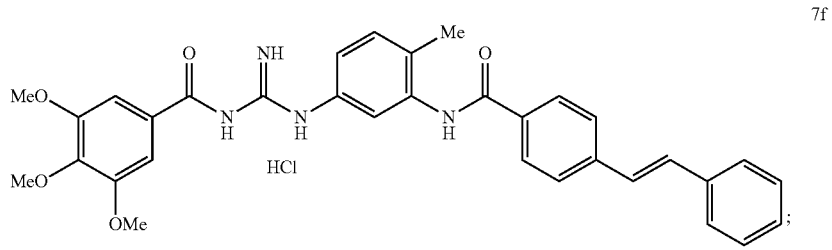

N—(N-(3-(4-benzylbenzamido)-4-methylphenyl)carbamimidoyl)-3,4,5-trimethoxybenzamide of the following formula:

(Compound 7g)

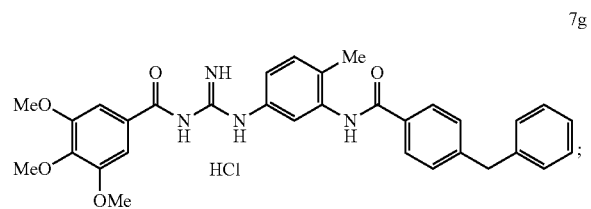

and

N—(N-(3-(4-(benzyloxy)benzamido)-4-methylphenyl)carbamimidoyl)-3,4,5-trimethoxybenzamide of the following formula:

(Compound 7h)

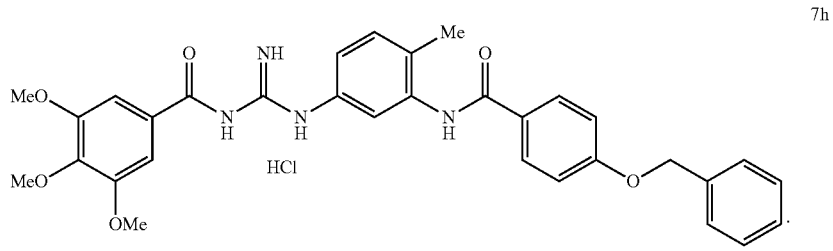

7. A medicinal product comprising the compound of formula (I) as claimed in claim 1.

8. A method for treating tumors associated with hyperactivation of the Hedgehog protein signalling pathway, the method comprising the step of administering the medicinal product as claimed in claim 7, wherein the tumors associated with hyperactivation of the Hedgehog protein signalling pathway are nerve tissue tumors (medulloblastomas, neuroectodermal primary tumors, glioblastomas, meningiomas and oligodendrogliomas), skin tumors (basal cell carcinomas, trichoepitheliomas), tumors of muscle and bone tissues (rhabdomyosarcomas, osteosarcomas) or tumors of other tissues (kidney, bladder, prostate, lung, stomach, pancreas).

9. A method for treating disorders of the neurodegenerative type comprising the step of administering the medicinal product as recited in claim 7, wherein the disorders of the neurodegenerative type are Parkinson's disease, Huntington's chorea, Alzheimer's disease, multiple sclerosis or motor neuron disease.

10. A method for treating diseases connected with cerebral development (holoprosencephaly), for treating cerebrovascular accident and cardiovascular accidents, as well as for diseases of the oligodendrocytes and Schwann cells, the method comprising the step of administering the medicinal product as recited in claim 7.

11. A method for in vitro modulating the renewal of human or animal stem cells, the method comprising the step of administering the medicinal product as recited in claim 7.

12. A method for treating diabetes, the method comprising the step of administering the medicinal product as recited in claim 7.

13. A pharmaceutical composition comprising as active principle, at least one compound of formula (I) as claimed in claim 1 and at least one pharmaceutically acceptable excipient.

* * * * *

UNITED STATES PATENT AND TRADEMARK OFFICE
CERTIFICATE OF CORRECTION

PATENT NO. : 8,981,149 B2  Page 1 of 1
APPLICATION NO. : 14/346538
DATED : March 17, 2015
INVENTOR(S) : Ruat et al.

It is certified that error appears in the above-identified patent and that said Letters Patent is hereby corrected as shown below:

In the Claims

Column 55,
Lines 10 through 17, "Compound 7a" should appear as follows:

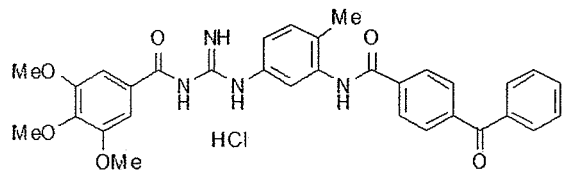

Signed and Sealed this
Twentieth Day of October, 2015

Michelle K. Lee
*Director of the United States Patent and Trademark Office*